(12) United States Patent
Stout et al.

(10) Patent No.: US 8,137,303 B2
(45) Date of Patent: Mar. 20, 2012

(54) VASCULAR ACCESS DEVICE CLEANING STATUS INDICATION

(75) Inventors: Marty L. Stout, South Weber, UT (US); Mark A. Crawford, Sandy, UT (US); Weston F. Harding, Lehi, UT (US); Austin Jason McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 499 days.

(21) Appl. No.: 11/745,359

(22) Filed: May 7, 2007

(65) Prior Publication Data
US 2007/0293818 A1 Dec. 20, 2007

Related U.S. Application Data

(60) Provisional application No. 60/798,517, filed on May 8, 2006.

(51) Int. Cl.
*A61M 1/00* (2006.01)
(52) U.S. Cl. ........... 604/31; 604/265; 604/318; 604/361
(58) Field of Classification Search ............. 604/31, 604/265, 318, 361
See application file for complete search history.

(56) References Cited

U.S. PATENT DOCUMENTS

| | | | |
|---|---|---|---|
| 3,650,093 A | 3/1972 | Rosenberg | |
| 3,667,916 A * | 6/1972 | Sliva et al. | 436/1 |
| 3,768,976 A | 10/1973 | Hu et al. | |
| 4,449,518 A * | 5/1984 | Konomura et al. | 600/133 |
| 4,764,111 A * | 8/1988 | Knierim | 433/5 |
| 4,765,588 A | 8/1988 | Atkinson | |
| 4,820,755 A * | 4/1989 | Webster | 524/88 |
| 4,834,706 A | 5/1989 | Beck et al. | |
| 5,053,339 A | 10/1991 | Patel | |
| 5,178,267 A * | 1/1993 | Grabenkort et al. | 206/210 |
| 5,251,873 A | 10/1993 | Atkinson et al. | |
| 5,295,657 A | 3/1994 | Atkinson | |
| 5,295,658 A | 3/1994 | Atkinson et al. | |
| 5,342,316 A | 8/1994 | Wallace | |
| 5,441,487 A | 8/1995 | Vedder | |
| 5,474,544 A | 12/1995 | Lynn | |
| 5,501,426 A | 3/1996 | Atkinson et al. | |
| 5,533,708 A | 7/1996 | Atkinson et al. | |
| 5,549,651 A | 8/1996 | Lynn | |

(Continued)

FOREIGN PATENT DOCUMENTS

EP 0 610 072 A1 8/1994

(Continued)

OTHER PUBLICATIONS

U.S. Appl. No. 11/745,357, Non-Final Rejection issued Sep. 11, 2009 by the United States Patent and Trademark Office, pp. 1-7.

(Continued)

*Primary Examiner* — Nicholas Lucchesi
*Assistant Examiner* — Scott Medway
(74) *Attorney, Agent, or Firm* — Mony R. Ghose; Kirton & McConkie

(57) ABSTRACT

A vascular access device for communicating with the vascular system of a patient may include a status indicator. The status indicator may detect and signal whether and to what extent at least a portion of the vascular access device has been cleaned.

12 Claims, 27 Drawing Sheets

U.S. PATENT DOCUMENTS

| | | | |
|---|---|---|---|
| 5,723,132 A | 3/1998 | Tseng et al. | |
| 5,769,781 A * | 6/1998 | Chappuis | 600/202 |
| 5,906,834 A | 5/1999 | Tseng | |
| 5,957,898 A | 9/1999 | Jepson et al. | |
| 6,017,318 A | 1/2000 | Gauthier et al. | |
| 6,039,718 A | 3/2000 | Niedospial, Jr. | |
| 6,171,287 B1 | 1/2001 | Lynn et al. | |
| 6,218,189 B1 * | 4/2001 | Antonoplos et al. | 436/1 |
| 6,261,282 B1 | 7/2001 | Jepson et al. | |
| 6,344,033 B1 | 2/2002 | Jepson et al. | |
| 6,463,335 B1 * | 10/2002 | Munch et al. | 607/129 |
| 6,511,728 B1 | 1/2003 | Bakos et al. | |
| 6,575,919 B1 * | 6/2003 | Reiley et al. | 600/567 |
| 6,585,691 B1 | 7/2003 | Vitello | |
| 6,595,964 B2 | 7/2003 | Finley et al. | |
| 6,651,956 B2 | 11/2003 | Miller | |
| 6,669,681 B2 | 12/2003 | Jepson et al. | |
| 6,730,113 B2 * | 5/2004 | Eckhardt et al. | 607/94 |
| 6,766,817 B2 | 7/2004 | da Silva | |
| 6,814,085 B2 | 11/2004 | Brattesani et al. | |
| 6,866,656 B2 | 3/2005 | Tingey et al. | |
| 6,878,131 B2 * | 4/2005 | Novacek et al. | 604/110 |
| 6,908,459 B2 | 6/2005 | Harding et al. | |
| 6,918,404 B2 | 7/2005 | da Silva | |
| 7,066,586 B2 | 6/2006 | da Silva | |
| 7,081,122 B1 * | 7/2006 | Reiley et al. | 606/185 |
| 7,105,715 B2 * | 9/2006 | Carlucci et al. | 604/361 |
| 7,232,253 B2 | 6/2007 | Isbitsky et al. | |
| 2002/0111577 A1 | 8/2002 | Sirimanne et al. | |
| 2002/0193752 A1 | 12/2002 | Lynn | |
| 2003/0114836 A1 | 6/2003 | Estes et al. | |
| 2004/0237785 A1 | 12/2004 | Neri | |
| 2005/0037498 A1 | 2/2005 | Ribi | |
| 2005/0137542 A1 * | 6/2005 | Underhill et al. | 604/361 |
| 2005/0256500 A1 | 11/2005 | Fujii | |
| 2006/0069305 A1 | 3/2006 | Couvillon, Jr. et al. | |
| 2006/0134728 A1 * | 6/2006 | MacDonald et al. | 435/34 |
| 2006/0287672 A1 | 12/2006 | McEwen et al. | |

FOREIGN PATENT DOCUMENTS

| | | |
|---|---|---|
| EP | 1 125 548 A1 | 8/2001 |
| GB | 2 379 253 A | 3/2003 |
| JP | 6-277118 | 10/1994 |
| WO | 99/47020 | 9/1999 |
| WO | 2004/114256 A2 | 12/2004 |

OTHER PUBLICATIONS

U.S. Appl. No. 11/745,357, Requirement for Restriction/Election issued Mar. 22, 2010 by the United States Patent and Trademark Office, pp. 1-7.

U.S. Appl. No. 11/745,357, Notice of Allowance issued Jun. 16, 2010 by the United States Patent and Trademark Office, pp. 1-6.

* cited by examiner

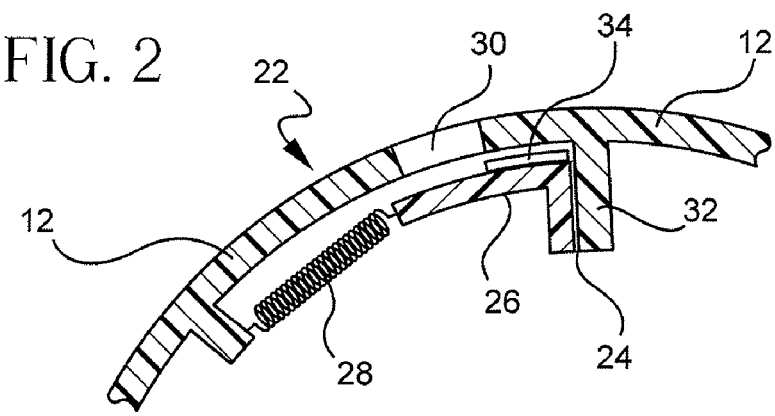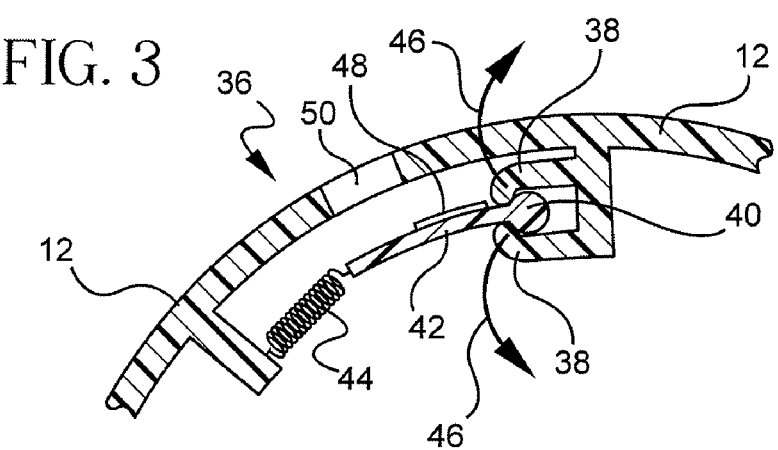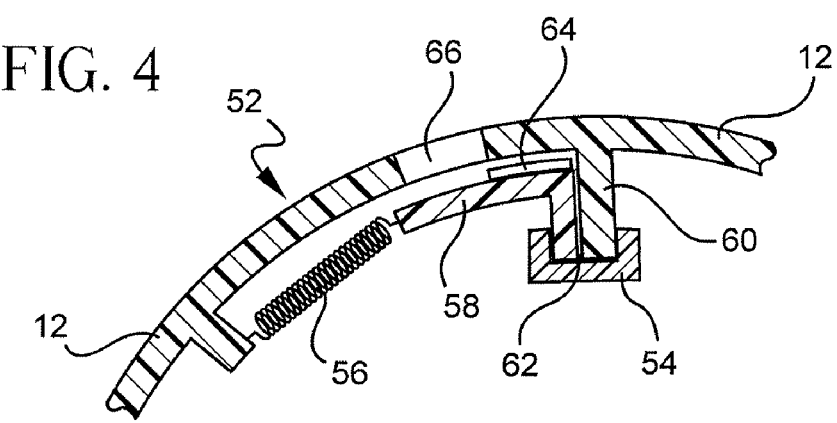

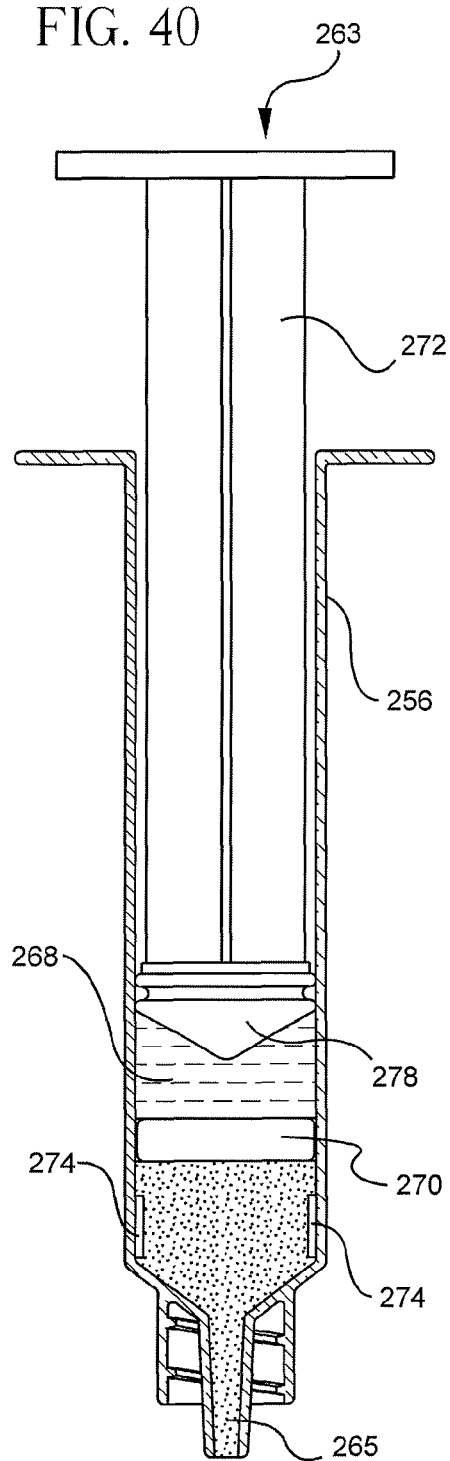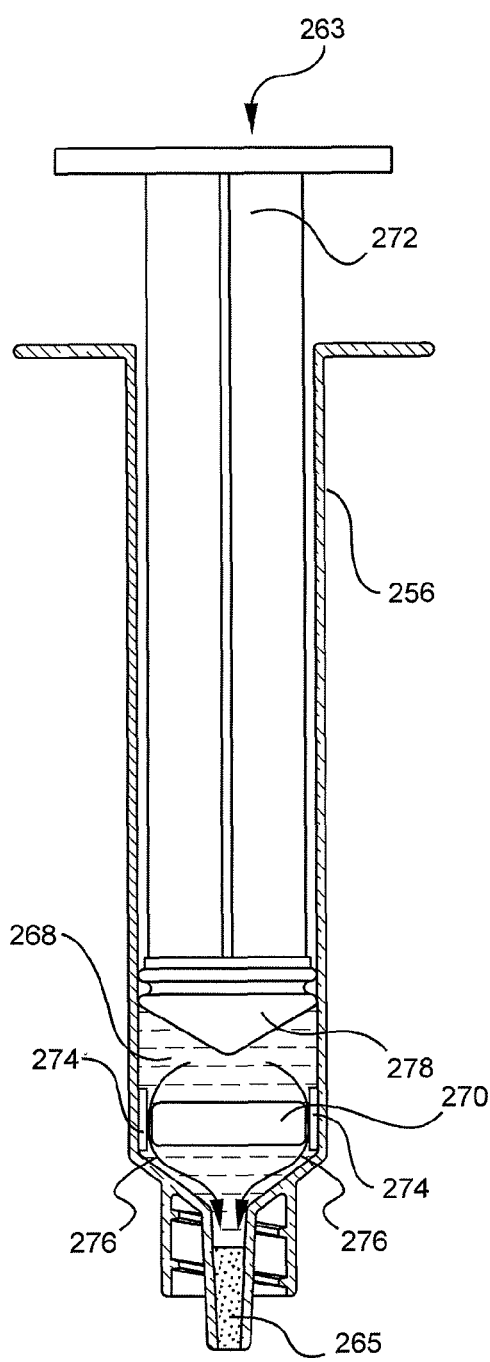

VASCULAR ACCESS DEVICE CLEANING STATUS INDICATION

RELATED APPLICATIONS

This application claims the benefit of U.S. Provisional Application No. 60/798,517, filed May 8, 2006, entitled VASCULAR ACCESS DEVICE STATUS INDICATION, and is incorporated herein.

BACKGROUND OF THE INVENTION

The present disclosure relates to infusion therapy with vascular access devices. Infusion therapy is one of the most common health care procedures. Hospitalized patients as well as home care patients receive fluids, pharmaceuticals and blood products via a vascular access device (VAD) that may be inserted at least partially into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy. A vascular access device is commonly a plastic catheter that is inserted into a patient's vein, but may include any device employed to access the vasculature, such as a catheter, a syringe, a Luer adapter, an intravenous (IV) set, bag, or devices attached thereto, a needle, or other related devices. The catheter may be from a few centimeters in length for peripheral access to many centimeters long for central access. A vascular access device may be inserted transcutaneously or may be surgically implanted beneath the patient's skin. A vascular access device may have a single lumen or multiple lumens for infusion of many fluids simultaneously.

The proximal end of the vascular access device commonly includes a Luer adapter to which other vascular access devices may be attached in order to form an extravascular system. For example, an administration set of one or more vascular access devices may be attached to a vascular access device at one end and an intravenous bag at the other. The administration set is a fluid conduit for the continuous infusion of fluids and pharmaceuticals. Commonly, an intravenous access device is a vascular access device that may be attached to another vascular access device. The IV access device closes the vascular access device and allows for intermittent infusion or injection of fluids and pharmaceuticals. An IV access device may comprise a housing and a septum for closing the system. The septum may be opened with a blunt cannula or a male Luer of a medical device.

Complications associated with infusion therapy may cause significant morbidity and even mortality. One significant complication is catheter related blood stream infection (CRBSI). An estimate of 250,000-400,000 cases of central venous catheter (CVC) associated BSIs occur annually in US hospitals. Attributable mortality is an estimated 12%-25% for each infection and a cost to the health care system of $25,000-$56,000 per episode.

Vascular access device infection resulting in CRBSIs may be caused by a non-sterile insertion technique or by pathogens entering the fluid flow path subsequent to catheter insertion. Studies have shown the risk of CRBSI increases with catheter indwelling periods. This is due to a risk of contamination with every access of the vascular access device via an upstream port or IV access device. When contaminated, pathogens adhere to the vascular access device or IV access device, colonize, and form a biofilm. The biofilm is resistant to most biocidal agents and provides a replenishing source for pathogens to enter a patient's bloodstream and cause a BSI.

Recent studies have shown a potential correlation between the use of IV access devices and CRBSI rates. An IV access device is designed to close another vascular access device lumen between uses. Closure of the vascular access device supposedly prevents pathogens from infecting the vascular access device and causing a CRBSI. Contamination of an IV access device during use may originate from a variety of sources including a non-cleaned septum, a contaminated male Luer, or a contaminated infusion fluid. The contamination may result in pathogen colonization and biofilm formation which may cause a CRBSI if the pathogens enter the bloodstream. The risk of IV device contamination increases over time and with each use of the device.

Before accessing an IV access device, the top surface of the septum or valve should be swabbed with an alcohol pad or other pad containing an antimicrobial agent. The swabbing cleans the surface of foreign material and disinfects the surface. If the top surface is not swabbed and allowed to fully dry prior to use, foreign matter and pathogens may be introduced to the interior of the device. The pathogens may colonize the device and catheter leading to biofilm formation. The pathogens of the biofilm may breakaway and enter the patient's bloodstream resulting in a CRBSI. To ensure the highest ratio of foreign matter and pathogens are killed, the alcohol or antimicrobial agent must be first applied and then allowed to fully dry. Unfortunately, a large percentage of accesses of IV access devices are completed without swabbing and drying the septum or valve top surface. Thus, what is needed are indicators to remind the operator to clean or replace the vascular access device to reduce the risk and occurrence of CRBSI.

BRIEF SUMMARY OF THE INVENTION

The present invention has been developed in response to problems and needs in the art that have not yet been fully resolved by currently available vascular access devices and intravenous (IV) access devices. Thus, these developed systems and methods provide a vascular access device, or IV access device, with a status indicator capable of communicating a passage of time from when the vascular access device was first placed into service, an amount of usage of the vascular access device while in service, and/or disinfection of the vascular access device.

A vascular access device for introducing a substance into a blood vessel of a patient includes a body with a lumen, a septum within the lumen, and a status indicator. The vascular access device may also include a second vascular access device with a proximal end and a distal end. The distal end of the second vascular access device is introduced into the blood vessel, and the vascular access device is a connector affixed to the proximal end of the second vascular access device. The status indicator provides an indication of elapsed time using a time sensitive adhesive, a color-changing substrate insulated with a variably transmissive or variably permeable layer, a fluid absorbing material in contact with a series of separated dye, a colored liquid and a material through which the colored liquid is transferred, a photochromic material which includes an oxidizable material and/or a septum which includes a slit and an adhesive for sealing the slit.

The status indicator additionally or alternatively provides an indication of usage of the vascular access device which includes a ratchet, a septum which includes an external surface and at least one removable layer of colored material on the external surface of the septum, a bar code, a radio frequency identification chip, and/or a piezoelectric crystal.

The status indicator additionally or alternatively provides an indication of vascular access device disinfection which includes a thermochromic material, a pH sensor, an alcohol sensor, a moisture sensitive compound, a colored substrate beneath a textured surface, a reservoir of colored liquid, a piezochromic material, a polymer that changes color in the presence of intense ultraviolet light, and/or a pathogen staining solution.

These and other features and advantages of the present invention will become more fully apparent from the following description and appended claims or may be learned by the practice of the invention as set forth hereinafter.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 2 is a cross section view of a status indicator with a time-sensitive adhesive.

FIG. 3 is a cross section view of a status indicator with snap arms.

FIG. 4 is a cross section view of a status indicator with a clamp.

FIG. 40 is a cross section view of a loaded dual-chamber syringe status indicator.

FIG. 41 is a cross section view of a partially ejected dual-chamber syringe status indicator.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
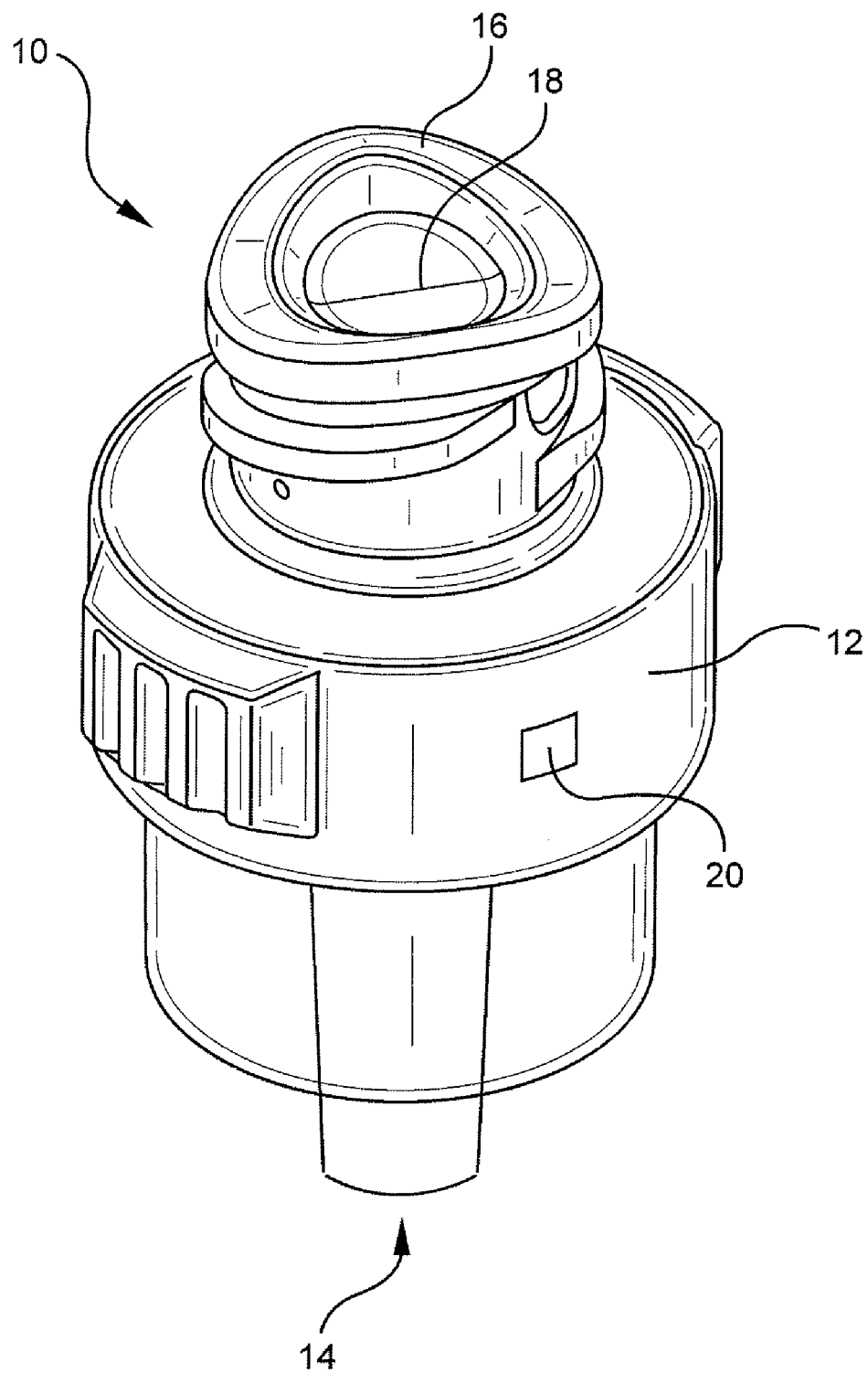
FIG. 1 is a perspective view of a vascular access device with a status indicator.

Referring now to FIG. 1, an intravenous (IV) access device and/or vascular access device 10 is used to introduce a substance into a blood vessel of a patient. As described herein, a vascular access device includes any device employed to access the vasculature, such as a catheter, a syringe, a Luer adapter, an IV set, bag, or devices attached thereto, a needle, or other related devices. The vascular access device 10 includes a body 12 with a lumen 14 and a septum 16 placed within the lumen 14. The septum 16 may have a slit 18 through which a device may introduce a substance into the lumen 14 of the vascular access device 10. The device 10 also includes a status indicator 20 which will be described with further detail in the following figures.

Referring now to FIG. 2, a status indicator 22 includes a time sensitive adhesive 24 attached to a movable member 26 and to the body 12 of a vascular access device 10. The movable member 26 is attached to the first end of a spring 28, and the second end of the spring 28 is attached to the body 12 of a vascular access device 10. The vascular access device 10 includes a window 30 through which the movable member 26 may be seen by an operator of the device 10 when the device 10 is in use.

An operator of the status indicator 22 may use the status indicator 22 to learn how long the device 10 has been in use. When the device 10 is first attached to another vascular access device, such as a catheter or other structure that is placed within the blood vessel or vein of a patient, an operator, such as a patient, a physician, a clinician, a nurse, or other healthcare professional, may allow the movable member 26 to be pulled away from a stationary member 32 towards the spring 28. Eventually, the time sensitive adhesive 24 will permit the movable member 26 to detach from the stationary member 32, causing the movable member 26 to shift its position towards the spring 28. When the movable member 26 is shifted from a first position to a second position, a red tag 34 will be placed within the viewing area of the window 30 through which the operator can see the red flag 34. Upon viewing the red flag 34, an operator will know that the device 10 has been in use for a specific period of a lapsed time.

Referring now to FIG. 3, a status indicator 36 has one or more snap arms 38 attached to the head 40 of a movable member 42. The movable member 42 is in turn attached at its tail to a first end of a spring 44, and the second end of the spring 44 is attached to a body 12 of a vascular access device 10. The plastic snap arms 38 engage the head 40 such that the movable member 42 is secured by the snap arms 38 for a predetermined amount of time. After a predetermined amount of time, the tension of the extended spring 44 causes the movable member 42 to pull upon the snap arms 38, which in turn causes the snap arms 38 to creep in a direction 46 opposite the head 40 of the movable member 42. Ultimately, the snap arms 38 will creep far enough such that the movable member 42 will be released from the snap arms 38 and will move from a first position in the snap arms 38 to a second position towards the spring 44 and away from the snap arms 38. In the second position, the movable member exposes a colored flag 48 through a window 50 of the body 12. When an operator of the vascular access device 10 sees that the flag 48 is exposed within the window 50, the operator will know that a given period of time has elapsed, indicating that the device 10 may need to be cleaned or replaced.

Referring now to FIG. 4, a status indicator 52 includes a clamp 54 which may be removed by an operator to initiate the sequence of steps illustrated in FIG. 2. Once the clamp 54 is removed from the status indicator 52, a spring 56 which is connected to the body 12 of a vascular access device 10 can pull a movable member 58 from a stationary member 60 over a period of time. After an elapsed, predetermined amount of time, an adhesive 62 holding the movable member 58 to the stationary member 60 will release, and the movable member 58 will move from a first position to a second position towards a spring 56. When the movable member 58 moves into the second position, a flag 64 or other visible, colored structure, will be exposed through a window 66. When the flag 64 is exposed through the window 66 of the device 10, an operator will know that a given period of time has elapsed, indicating that the device 10 may need to be cleaned or replaced.

The clamp 54 shown in FIG. 4 permits an operator to initiate the timing sequence of the status indicator 52 at any point in time. By permitting the operator to have control over when the status indicator is engaged by removing the clamp 54, an operator may choose to either engage the status indicator 52 upon first removing the device 10 from its sterile packaging, upon first attaching the device 10 to another vascular access device, or upon first using the attached device 10 by inserting a needle or other member to introduce a substance through the device 10 into a blood vessel of a patient.

Figure 5:
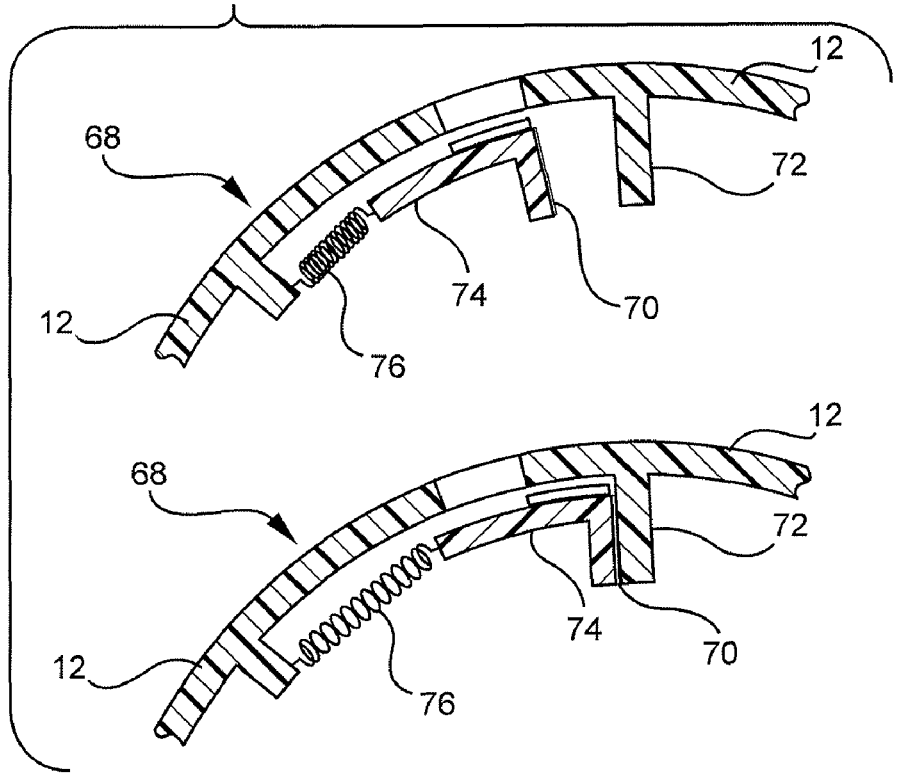
FIG. 5 is a cross section view of a set and unset adhesive status indicator.

Referring now to FIG. 5, a status indicator 68 may be delivered to an operator within its packaging such that an adhesive 70 is not yet attached to a stationary member 72. At any point after removing the device 10 from its packaging, an operator may engage or set the status indicator by pressing or otherwise placing a movable member 74 containing the time sensitive adhesive 70 against the surface of the stationary member 72. When the status indicator 68 is set by the operator, the operator initiates a time sequence by which the movable member 74 is pulled with a spring 76 in a direction opposite the bound surfaces of the movable member 74 and the stationary member 72.

Figure 6:
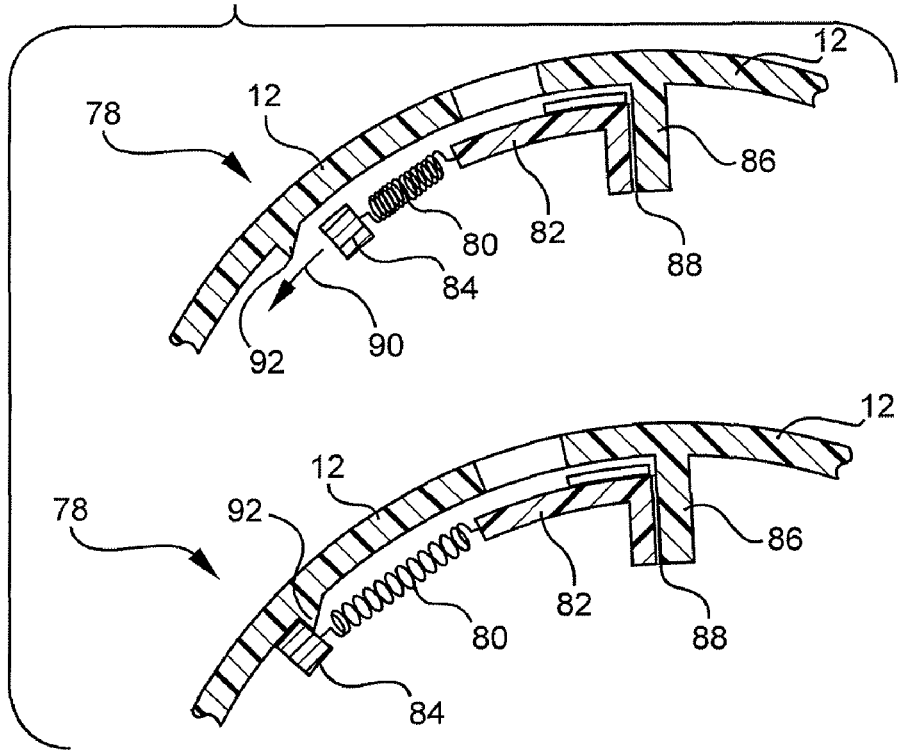
FIG. 6 is a cross section view of a set and unset spring anchored status indicator.

Referring now to FIG. 6, a status indicator 78 may come disengaged on a vascular access device 10 when the device 10 is still in its sterile packaging. Similar to the status indicator 68 of FIG. 5, a user may engage the status indicator 78 of FIG. 6 at any desired point of device 10 operation. A spring 80 is compressed in a state where no tension or force is placed upon the spring 80. The spring 80 is attached on a first end to a movable member 82 and on a second end to an anchor 84. The movable member 82 is attached to a stationary member 86 by means of a time sensitive adhesive 88. The anchor 84 may be set by an operator by moving the anchor 84 in a direction 90 opposite the direction of the movable member 82. Upon moving the anchor 84 along a certain distance in the direction 90, the anchor 84 is engaged with a notch 92. When the anchor 84 is fully engaged with the notch 92, an appropriate amount of tension and force is placed upon the spring 80 such that the movable member 82 will detach from the stationary member 86 after an appropriate predetermined amount of time, which indicates that the device 10 has been in operation for an appropriate amount of time.

Figure 7:
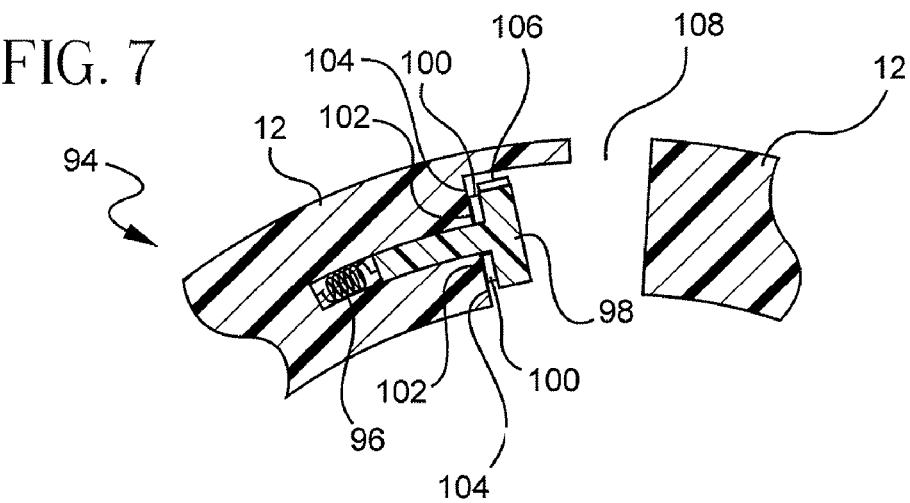
FIG. 7 is a cross section view of a compression spring status indicator.

Referring now to FIG. 7, a status indicator 94 includes a compression spring 96 attached on a first end to the body 12 of the device 10 and on a second end to a movable member 98. The movable member 98 is attached on a bottom surface 102 to a top surface 104 of the body 12 of the device 10. The compression spring 96 is compressed while the movable member 98 is adhered to the body 12. After a predetermined amount of time, the adhesive 100 will release the movable member 98 from the body 12 under the pressure and force of the compression spring 96. When moved, the movable member 98 will expose a flag 106 within a window 108 through which an operator may see the flag 106. When the operator sees the flag 106 through the window 108, the operator will know that the device 10 has been in use for the predetermined amount of time.

Any one of the status indicators of FIGS. 2 through 7 can be initiated by an operator in any number of ways when the device 10 is put into service. In one embodiment, the members may start together with a clamp that takes the load from the adhesive. The clamp is then removed at the start of service. In another embodiment, the members start together, but a spring is not loaded until the start of service. In another embodiment, an operator presses the two members together at the start of service.

Any of these actions initiating the start of service for any of the status indicators discussed above can be coupled to other actions which are commonly performed with a vascular access device. For example, a dust cover protecting certain structures on the vascular access device 10 may be removed after the device 10 is removed from its sterile packaging or after the vascular access device 10 is attached to another device. The dust cover may be removed by pulling the dust cover from a surface of the body 12 of the vascular access device 10 or by twisting and pulling the dust cover from the device 10. The device 10 may also be removed from the package, and a portion of the package may cause a status indicator to begin the time sequence that places it in service. Further, as the dust cover is removed, a clamp may be removed with the dust cover, a spring may be loaded with the dust cover, or a movable member may be placed into contact with a stationary member. Any other action performed by an operator of the device 10 can be combined to engage or disengage a status indicator.

The status indicators of FIGS. 2 through 7 may include any form of visual or mechanical indication as shown by example with the red flag 34 of FIG. 2. The flag 34, or form of visual or mechanical indication, may be any size, shape, or color and may include any mechanical structure capable of indicating any lapsed period of time to an operator. In addition, multiple status indicators or multiple flags may be used in a single device 10. In one embodiment, a device 10 includes a movable member with multiple flags indicating multiple periods of time that have elapsed.

In another embodiment, multiple movable members are attached to one or more stationary members using multiple time sensitive adhesives of varying strengths and or amounts. The multiple adhesives release at different time intervals, causing each of the multiple movable members to be released in sequence and thus illustrating that certain time periods have elapsed to an operator. For example, a first movable member with a weak adhesive or an adhesive in a small amount, may first disengage from a stationary member to show an operator that 12 hours have elapsed since the device 10 was placed in service. A second movable member attached to a stationary member with a stronger adhesive than the first movable member or attached to a stationary member with a greater amount of adhesive may later detach from the stationary member indicating to an operator that 24 hours have elapsed since the device 10 was placed in service. This sequence may occur for a third and subsequent movable members to indicate to an operator that various periods of time have elapsed.

Figure 8:
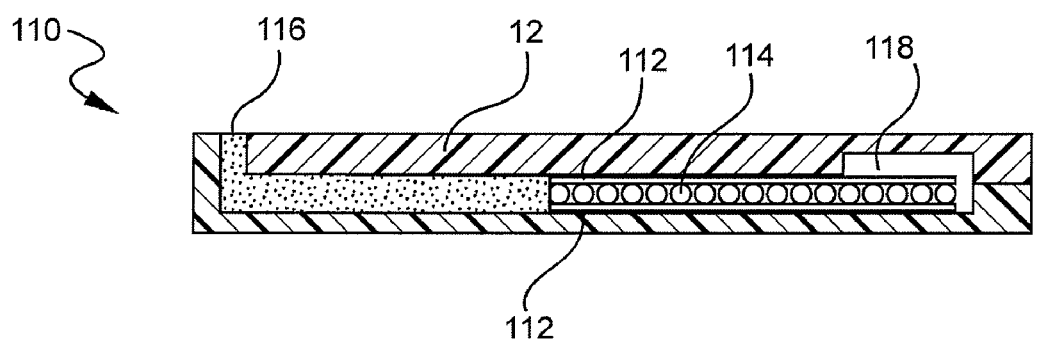
FIG. 8 is a cross section view of a status indicator with a wick and dye.
Figure 9:
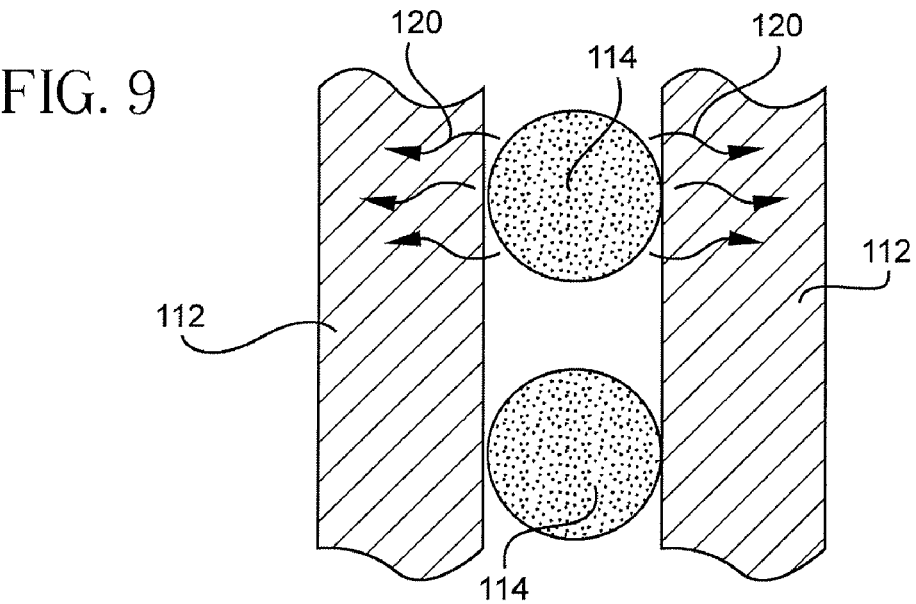
FIG. 9 is a cross section view of the wick and dye of FIG. 8.
Figure 10:
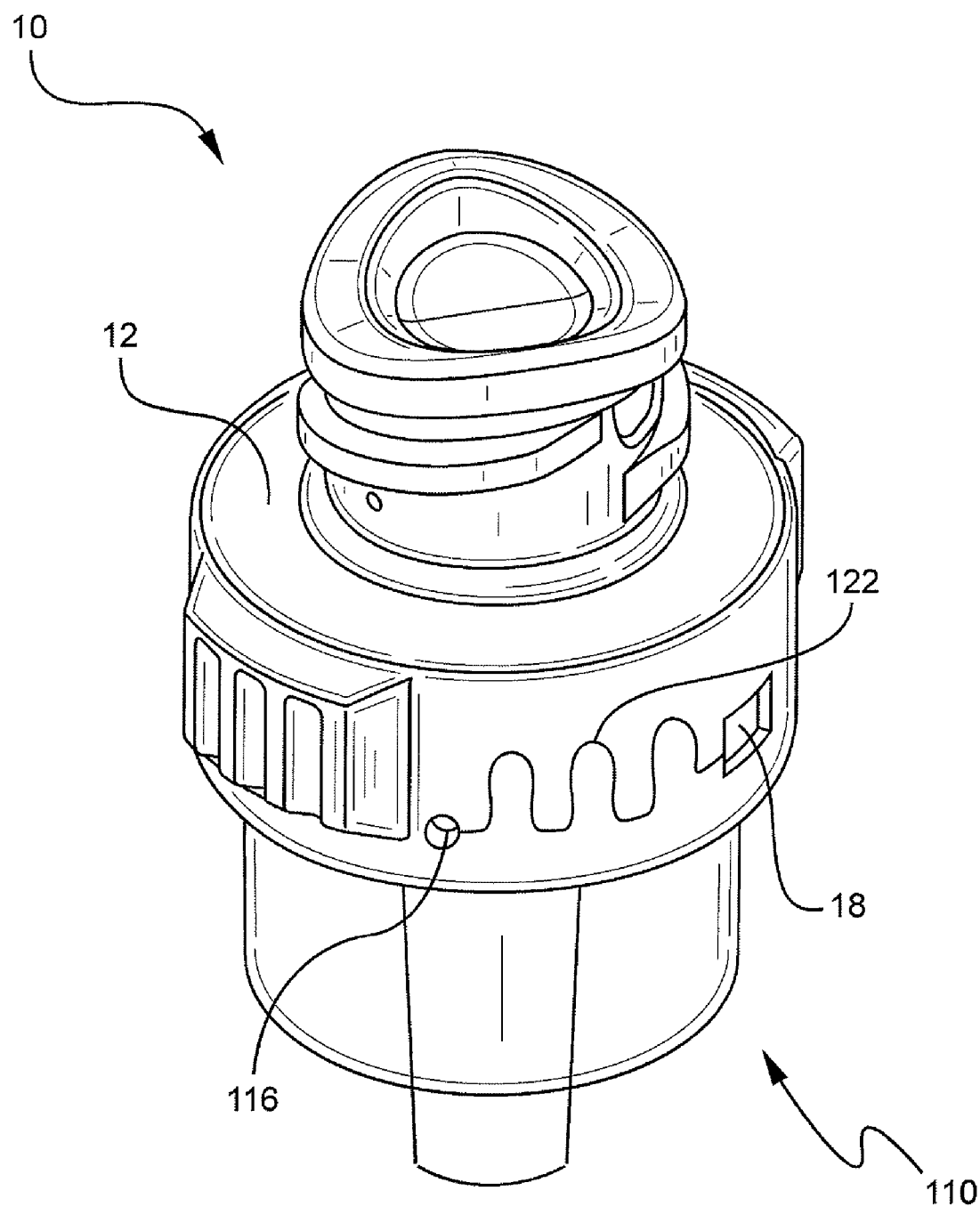
FIG. 10 is a side view of the status indicator of FIG. 8 on the surface of a vascular access device.

Referring now to FIGS. 8 through 10, a status indicator 110 includes a fluid absorbing material or a wick 112 and a series of separated dye 114. The wick 112 is in contact with the dye 114 as shown in the cross section view of the status indicator 110 which is placed on the body 12 of the vascular access device 10. The status indicator 110 also includes an open port 116 to which a catheter or other fluid delivery system or device is attached. For example, a catheter attached to an IV bag delivers water or saline to the open port 116, delivering a constant supply of saline or water to the wick 112. In the alternative, the device may include an exterior fluid reservoir which is activated upon usage of the device. As time passes, the capillary forces of the wick 112 draw water further along the length of the wick 112. As the water is drawn along the wick 112, the dye 114 core is wetted, and the color of the water soluble dye 114 leaches through the wall of the wick 112 such that it is visible on the outer surface of the wick 112. The wetted dye is visible through a viewing window 118 to an operator. As used above and as mentioned throughout this description and the claims, "usage" includes any use of a vascular access device or any structure in communication with the device, including any use of or interaction with the device, including disinfection, by a healthcare provider or other individual or with the environment after the vascular access device is removed from its manufacturer packaging.

Referring now to FIG. 9, a cross section view of the wick 112 and water soluble dye 114 is shown. As the wicking material or wick 112 is wetted, the dye 114 is dissolved and color migrates to the wicking material in a direction 120.

Referring now to FIG. 10, the status indicator 110 of FIG. 8 is shown embodied on the surface of a vascular access device 10. The status indicator 10 shows the port 116 that is open to receive a fluid supply. The status indicator 110 also shows a serpentine path 122 through which the wicking material 112 and dye 114 travel. The entire length, or any portion, of the path 122 may be viewable through the body 12 of the device 10 to an operator. The viewing window 118 of the status indicator 110 as shown in FIG. 10, permits the operator to see when the dye 114 at the end of the path 122 has been dissolved and has migrated to the wick 112 in the viewing window 118. When the dye 114 is seen in the viewing window 118, an operator will know that a predetermined amount of time has elapsed. The operator will then know that the operator should clean and/or replace the device 10.

In one embodiment, the wicking material 112 is a weave of fabric or a paper wick with a water soluble dye core. In another embodiment, the path 122 of the wick 112 and the dye 114 is not serpentine. Rather, the path 122 is a straight line. The serpentine path 122 is preferably spaced and has an adequate length to cover an entire desired predetermined time period for the status indicator 110. The path may also wrap around the entire device 10 in multiple revolutions. In another embodiment, the wick 112 is visible along the entire length of its path. In another embodiment, the wick 112 is visible at discreet points along the length of the path. In the preceding two embodiments, the status indicator preferably includes marks on the surface of the body 12 of the device 10 which indicate that various amounts of time have elapsed since the device 10 was placed in service. As the dye dissolves along the path, the various time indicator points are reached and are visible to an operator. In another embodiment, the dye 114 comes in various shapes, sizes, and colors. For example, along the path 122 a first series of dye 114 may be colored green to indicate a first 12 hour period, a second series of dye 114 are colored yellow to indicate a second 12 hour period from hour 12 to 24 and a third series of dye may be colored red to indicate a third 12 hour period from hour 24 to 36. When the path turns red, an operator will know that the device should soon or immediately be cleaned or replaced. The thickness and width of the wick material and dye and the size and spacing of the channel or path in which the wick and dye are placed may be varied in order to adjust the rate and visibility at which the dye is dissolved and displayed to an operator along the path.

Figure 11:
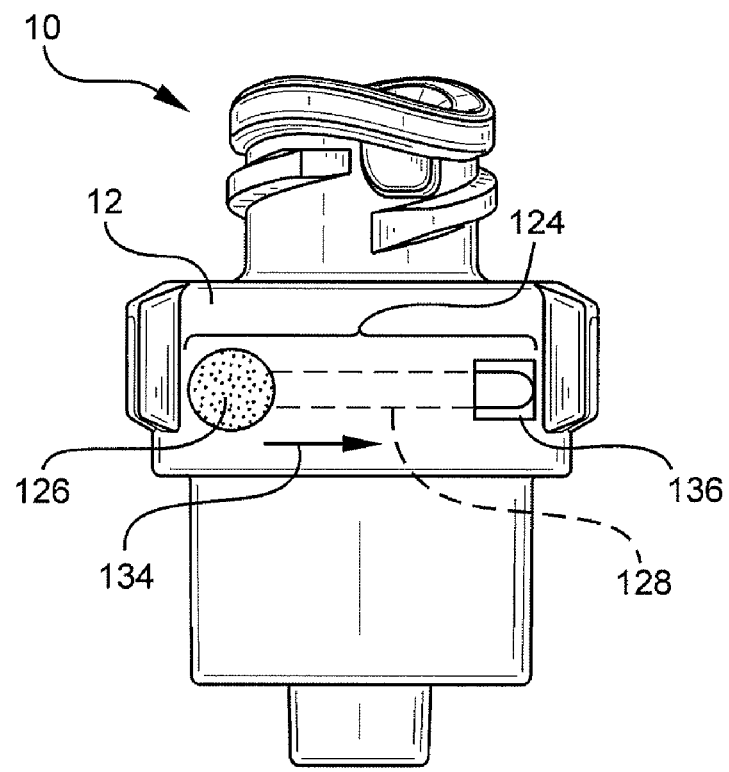
FIG. 11 is a side view of a status indicator with a reservoir of colored liquid on a vascular access device.

Referring now to FIG. 11, a status indicator 124 of a vascular access device 10 includes a colored liquid 126 and a material 128 placed in a channel 130 through which the colored liquid 126 is transferred.

Figure 12:
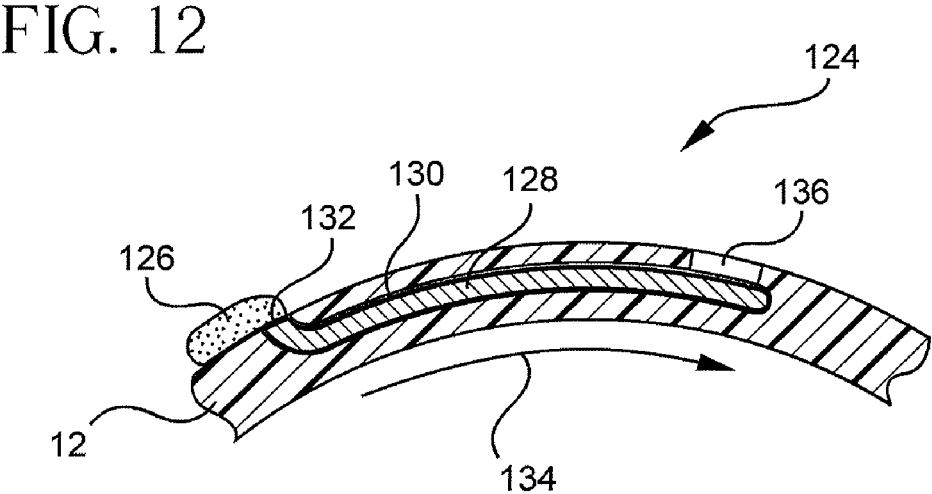
FIG. 12 is a cross section view of the reservoir of FIG. 11.

Referring now to FIG. 12, a cross section of the reservoir of colored liquid 126 of FIG. 11 is shown located on the exterior surface of the body 12 of the device 10. A seal 132 prevents the colored liquid 126 from being absorbed by the material 128 until an operator exerts pressure upon the reservoir of liquid 126. When an operator places pressure upon the colored liquid 126, the seal 132 is broken and the colored liquid 126 is permitted to travel in a direction 134 along the material 128 until the colored liquid 126 is visible in a window 136 to an operator.

As shown in FIG. 12, the status indicator 124 is integrated into the device 10. In another embodiment, the status indicator 124 is a label having a colored ink or colored oil as the colored liquid 126, and the label is attached to the device 10. In this embodiment, the colored ink or oil 15 initially contained in a reservoir that is obscured from view via a mask of the label. The ink or oil is then exposed to a porous or absorbent material. The material is designed to wick the ink or oil at a specified rate. Activation of the wicking may be accomplished by an operator compressing the reservoir as discussed above. The compression, however, may not be accomplished by the operator's fingers. Rather, the compression of the reservoir may be initiated in conjunction with use of the device 10 as it is placed in service or upon any other event capable of acting upon the reservoir. For example, the compression is caused by removing a dust cover from the device 10. As another example, the compression is caused when the device 10 is attached to another vascular access device providing access to a blood vessel of the patient. By twisting the device 10 onto another device, the force required to twist and attach the two devices together may also simultaneously compress the reservoir to initiate the travel of the colored ink or oil along the absorbent material. At least one point equivalent to a desired elapsed time of wicking, the colored material is exposed to view in at least one viewing window to an operator. In this manner, the material changes color and the operator is able to visualize the time based color change.

Figure 20:
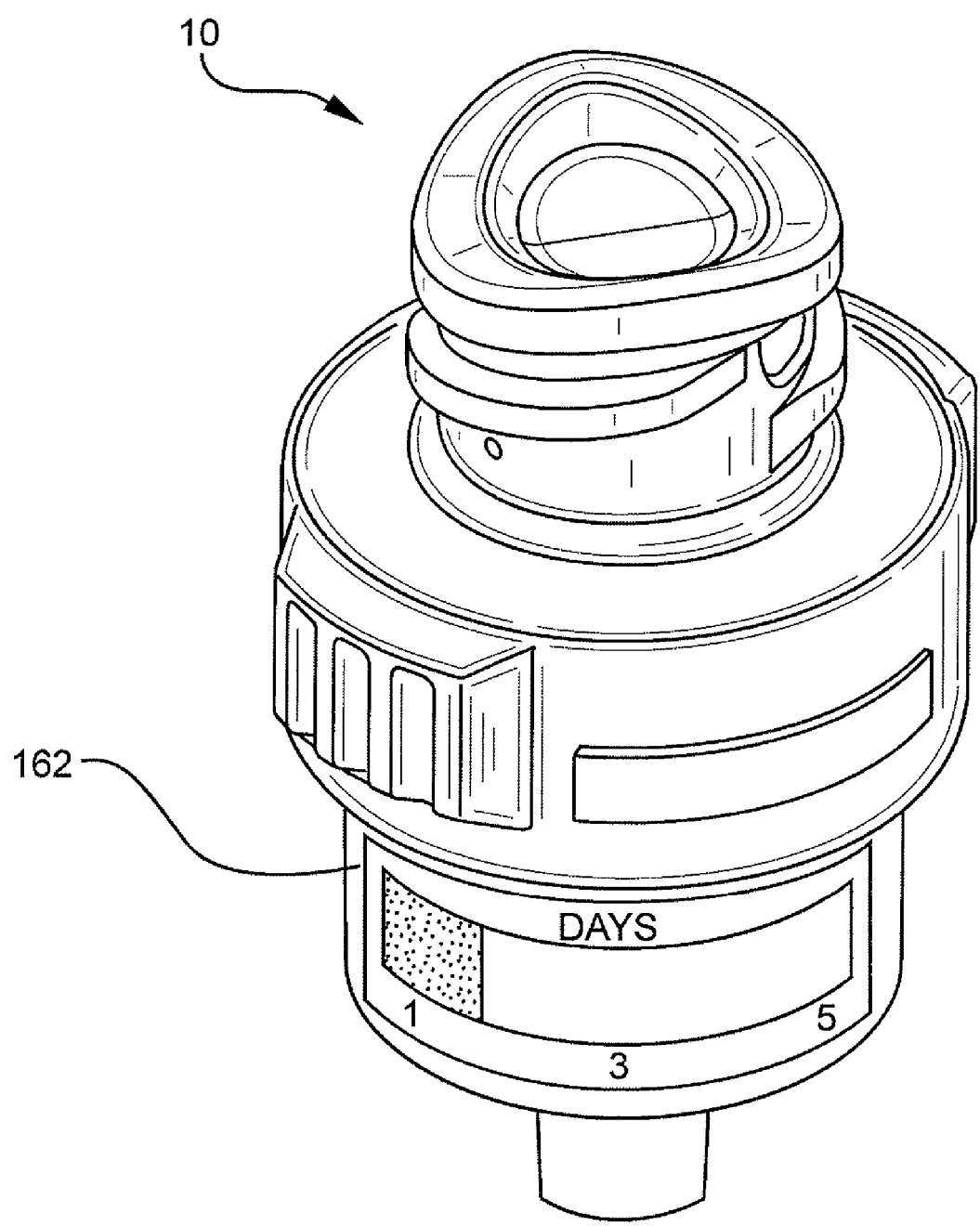
FIG. 20 is a perspective view of a label as a status indicator attached to a vascular access device.

Referring now to FIG. 20, a label 162 as previously discussed, is attached to a vascular access device 10. The label 162 shows an elapsed time period in numbers of days by advancing a strip of color across the label 162. In one embodiment, the label may be integrated into the device 10.

Figure 13:
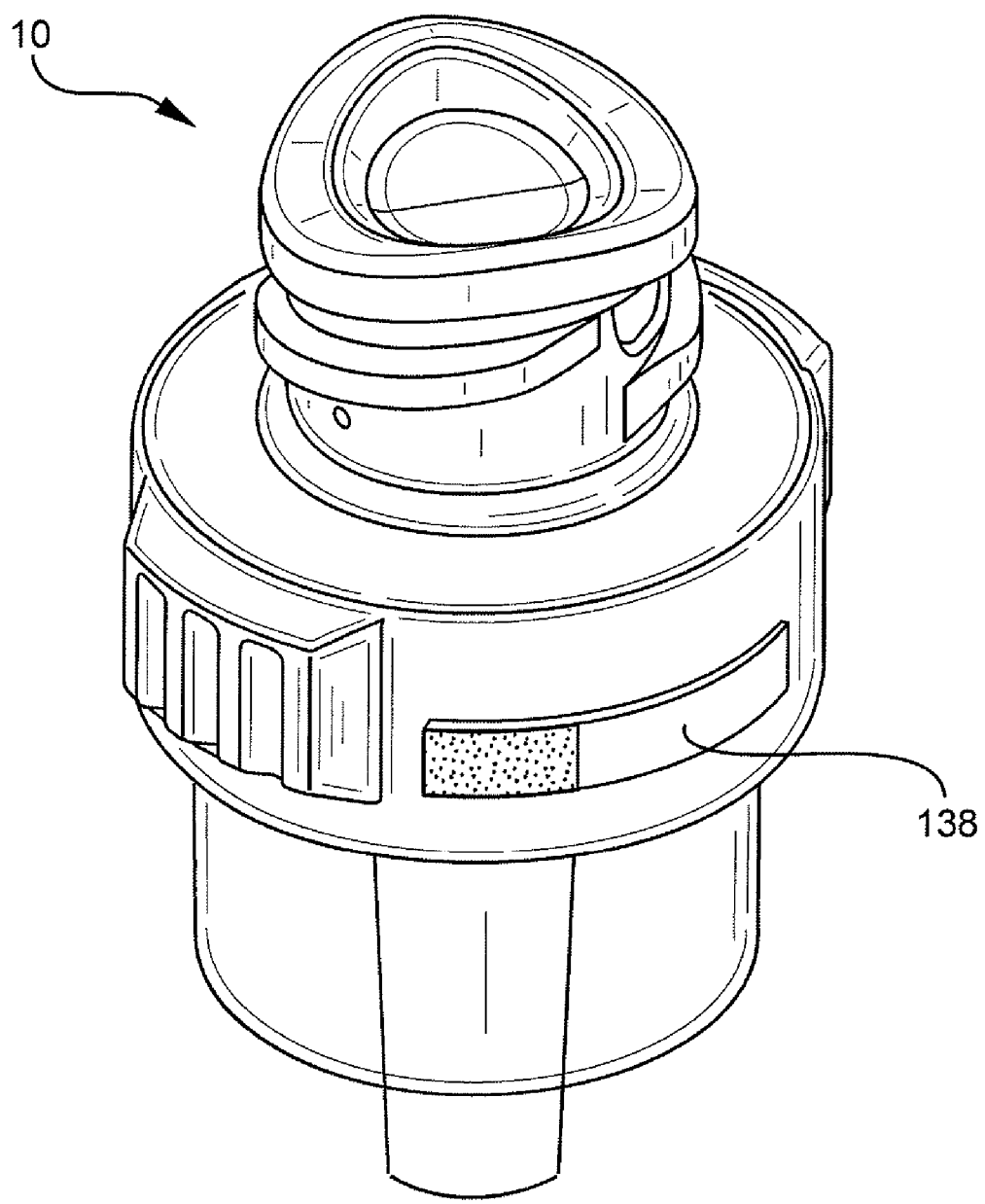
FIG. 13 is a side view of a strip status indicator on a vascular access device.

Referring now to FIG. 13, a status indicator 138 is a label adhered to the exterior surface of the device 10.

Figure 14:
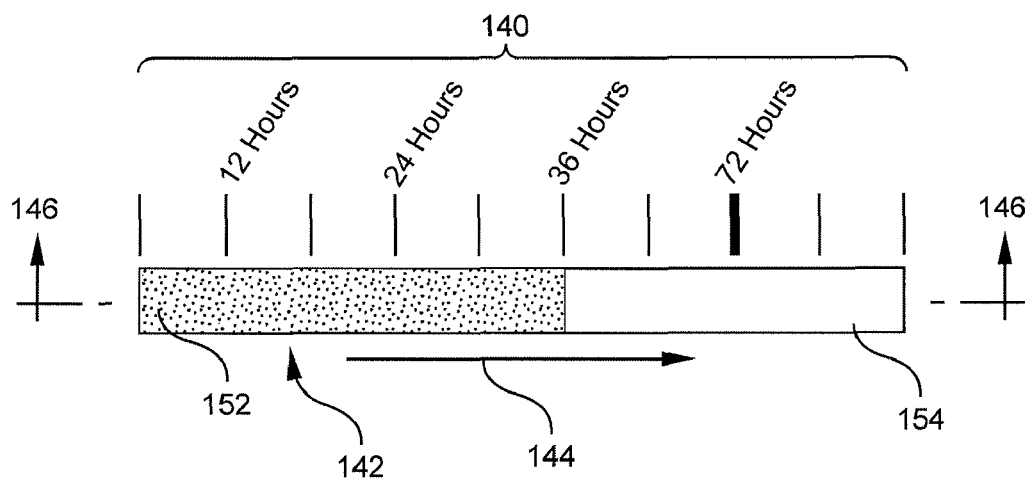
FIG. 14 is a close up side view of the strip status indicator of FIG. 13.

Referring now to FIG. 14, the status indicator 138 is shown in further detail. The label, or strip, of the status indicator 138 indicates various time periods 140 along its length. The time periods 140 are divided as follows: 12 hours, 24 hours, 36 hours, and 72 hours. When any of these given periods of time have elapsed as displayed by the status indicator 138 to an operator, the operator may either clean or remove and replace the device 10 depending on the specific needs of the patient and the environment in which the device 10 is used. The strip 142 is a multi-layered strip that is sensitive to light. When exposed to light, the strip 142 slowly begins to change color initially at a first end and then the color change advances to a second end of the strip 142 in a direction 144. The rate at which the color travels in the direction 144 may be modulated or adjusted or tuned, by overlaying a semi-transparent layer over a color changing substrate as shown in FIG. 15.

Figure 15:
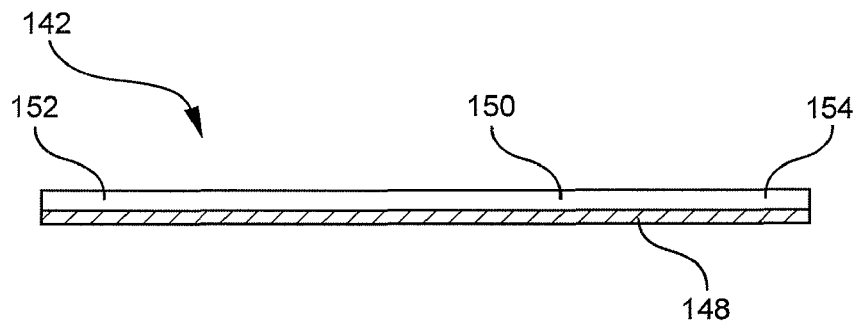
FIG. 15 is a cross section view of the strip of FIG. 14 taken along lines 146-146 of FIG. 14.

Referring now to FIG. 15, a cross section of the strip 142 of FIG. 14 is shown along lines 146-146. The cross section of the strip 142 reveals a color changing substrate 148 and a variably transmissive insulating layer 150 on top of the color changing substrate 148. The variably transmissive layer 150 has a higher degree of transmissivity to light at its first end 152 and a lower amount of transmissivity to light at its second end 154. Between end 152 and end 154, the degree of transmissivity to light of the layer 150 is graded from a higher to a lower amount of transmissivity. Thus the transmissive layer 150 permits light to communicate with the color changing layer 148 at a faster rate at end 152 than the light would communicate at the end 154. This permits the status indicator 148 to show an earlier color change at end 152 than the color change at end 154. The earlier color change is shown in FIG. 14 as a colored band beginning at end 152 and traveling through the 12 hour, 24 hour, 36 hour marks. However, because end 154 of FIG. 14 has a lower level of transmissivity to light the light has not yet been permitted to communicate with the color changing substrate 148, and the strip 142 does not yet show a color change at end 154.

In one embodiment, as shown with reference to FIGS. 13 through 15 above, the status indicator 138 is sensitive to light. In another embodiment, the status indicator is sensitive to oxygen. When exposed to oxygen, the strip of the status indicator begins to slowly change color. In this embodiment, rather than having a semi-transparent layer 150, the strip includes a semi-permeable layer over the color changing substrate 148. The semi-permeable layer is permeable to oxygen. The semi-permeable layer is variably permeable such that the first end of the strip will change color before a second end of the strip changes color, indicating a change in time during the use of the device 10. The color change will begin at one end of the strip, and proceed along the length of the strip during the period of elapsed time. In this manner, the position of the boundary between the colored and the non-colored portions of the strip becomes an indicator of how long the strip has been exposed to oxygen.

In one embodiment, a light or oxygen sensitive strip is mounted on an adhesive backing and applied to any time sensitive device 10. The device is stored in a light or oxygen proof package to ensure that the strip does not initiate its time sequence until after the package is opened. Many of the embodiments discussed with reference to FIGS. 13 through 15 appear much like a temperature-sensitive strip used in a fish tank. However, the colored band or strip indicates the passage of time rather than a change in temperature. The principals discussed in these embodiments may be applied to indicate the passage of time, an amount of use of the device 10, or the disinfection of the device 10.

The oxygen sensitive material discussed above may be an oxidizable compound that is covered by a substrate. The oxidizable compound may be a metal such as aluminum, silver, or magnesium. When oxidized, the metal may turn a dark color or exhibit some other visual change. In one embodiment, a layer that is semi-permeable to oxygen may cover the oxidizable compound. In another embodiment, the compound is compounded directly into the layer. The layer is designed to have an oxygen permeability rate controlling the timing of the oxidation of the metal. The layer and/or oxidative compound may contain an anti-oxidant to control the timing of oxidation. The anti-oxidant will delay the oxidation reaction until the anti-oxidant is consumed. The oxidative compound and layer may be incorporated directly into the device 10. Alternately, the oxidative compound and layer may be attached by adhesive to the device 10. Alternatively, the oxidative compound and layer may be incorporated into a disk or other structure that can be attached to the exterior surface of the device 10. Multiple labels, disks, and/or bands of varying lengths may be used in combination on a single device 10 to indicate the passage of multiple periods of time.

Figure 16:
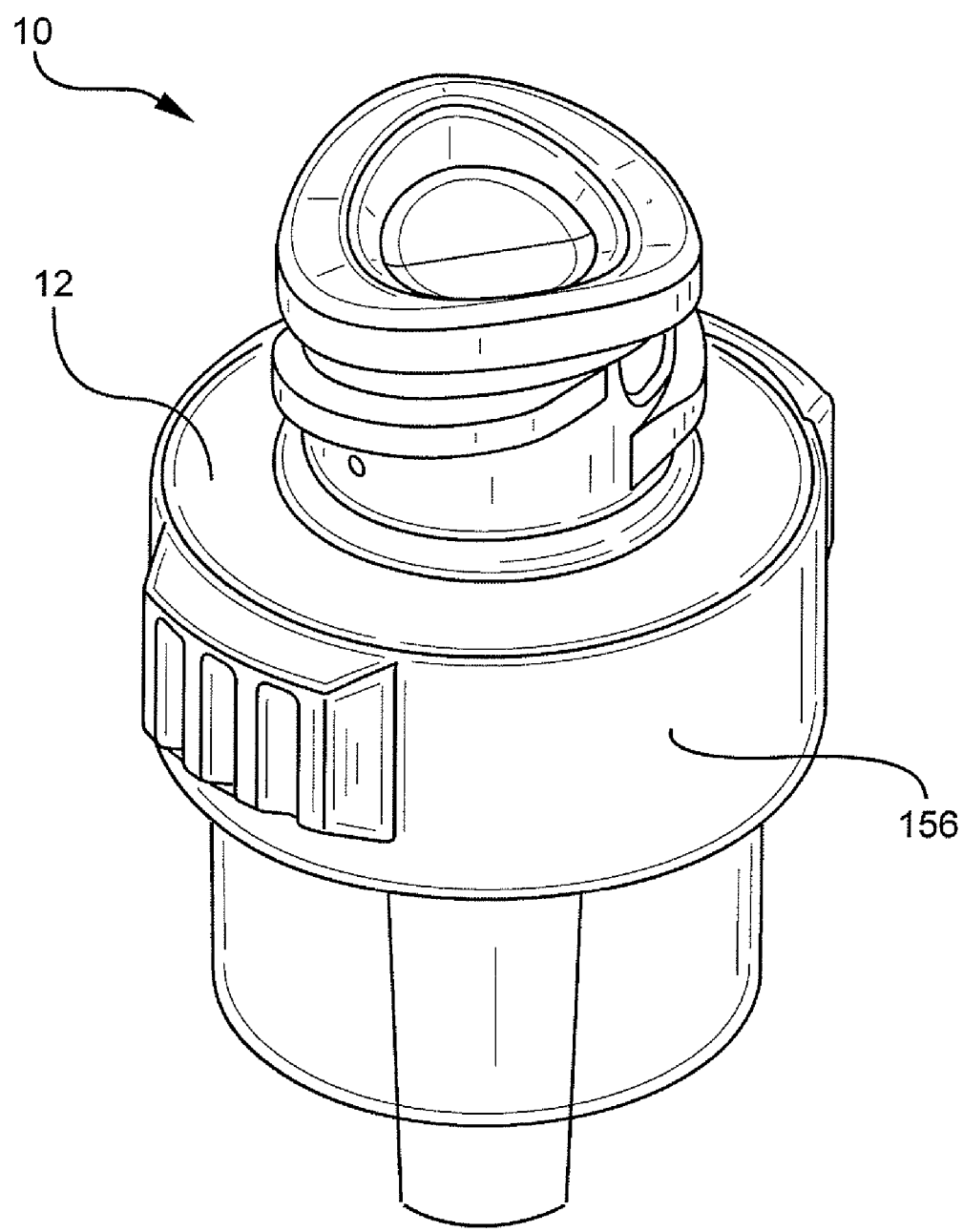
FIG. 16 is a perspective view of a lightened photochromic vascular access device as a status indicator.

Referring now to FIG. 16, a status indicator 156 includes a photochromic material forming the body 12 of a device 10. The photochromic material 156 is a visual status indicator that shows a distinct change in color from when the device 10 is first placed into service at initial use to a specific lapse of time as mentioned above. For example, the photochromic material 156 starts as a clear or white color upon initial use of the device 10. After the device 10 has been attached to a vascular access device or otherwise placed in service for 24 hours, the photochromic material 156 changes to a dark color 158 as shown in FIG. 17.

Figure 17:
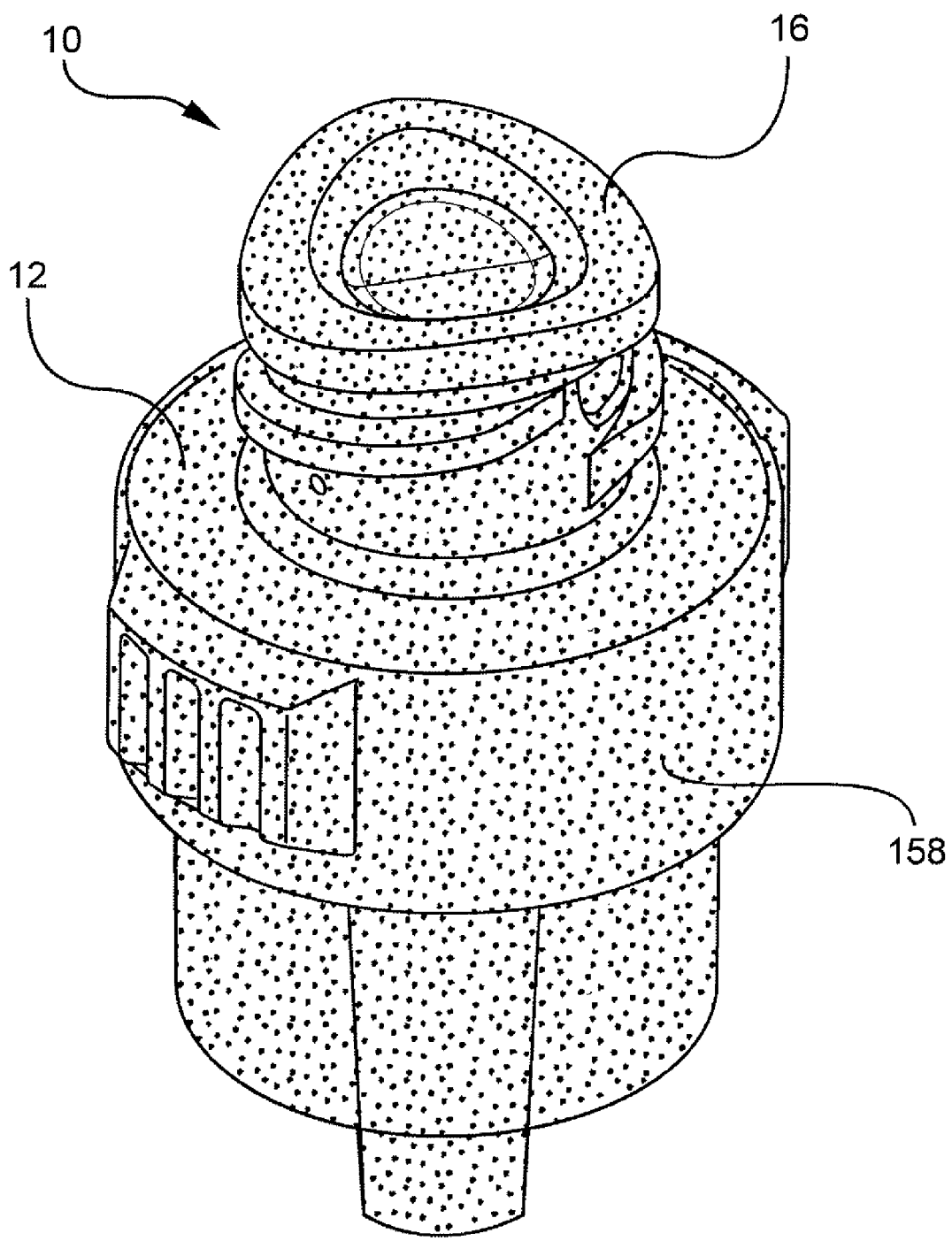
FIG. 17 is a perspective view of a darkened photochromic vascular access device as a status indicator.

Referring now to FIG. 17, the dark photochromic material 158 of the device 10 indicates to an operator that the device 10 has been placed in service for at least 24 hours and has reached an infection risk threshold. The operator may then clean or replace the device 10.

The color change of the photochromic material 156 and 158 of FIGS. 16 and 17 may be accomplished in a variety of embodiments. In one embodiment, a photochromic dye is incorporated directly into the device 10, to any portion thereof, or to any structure attached thereto. Photochromic materials may be used to, for example, indicate a passage of time during which a photochromic material has been exposed to light or the lack thereof, indicate whether and to what extent a photochromic material has been disinfected, and/or indicate whether and to what extent a photochromic material has been properly cleaned. Photochromic dyes are commonly used compounds for non-medical device applications such as eyeglasses and printing. When sunlight or ultraviolet (UV) radiation is applied, the dye becomes excited and the molecular structure is changed allowing a color to appear.

Photochromic materials include a colorless isomer that contains a spiro carbon atom. This carbon atom is $SP^3$-hybridized and serves to separate the molecule into two halves. Because of the highly localized pi systems that are separated by a $SP^3$-hybridized carbon, all absorption is in the UV part of the spectrum with none in the visible part of the spectrum, and hence the molecule appears colorless. When the molecule absorbs UV light, the spiro carbon atom opens. The molecular structure then changes to one of extended conjugation and the molecule absorbs light in the visible region. Many colors are possible through the mixing or four base colors: blue, yellow, purple and orange/red. UV absorbing compounds may be used in conjunction with the photochromic dyes to extend the time of color shift.

The sensitivity of the ultraviolet material 158 may be modified and/or modulated in order to provide a material that only changes color when in the presence of an ultraviolet light of very high intensity. Thus an ultraviolet light wand or other light source may be applied to the high intensity UV sensitive material 158 in order to change its color. After the color is changed and the intense light source is removed, it may return back to an original color after a predetermined amount of time. The intense source of ultraviolet light may be applied to the material just prior to, during, or after disinfection of the material.

A light source may be provided not only to change the color or provide some other visual change of a vascular access device, but a UV light source may additionally or alternatively be used to sterilize or disinfect the device. UV rays or various intensities and wavelengths may be used to kill or harm bacteria or pathogens on the device in order to disinfect the device. In such an embodiment, a UV wand or other device may be placed by a healthcare provider into communication with at least a portion of a vascular access device in order to disinfect the device. The wand may remain in communication with the vascular access device until the device is disinfected. After disinfection occurs, the healthcare provider may remove the UV wand.

A light source may also be used to confirm whether all or a significant number of pathogens have been killed. For example, a photochromic material may require a completion of a color change in order to indicate that all or a significant number of bacteria and pathogens have been completely killed on the light sensitive material. An operator is then able to confirm whether the operator remembered to sterilize or disinfect the device 10. For example, the absence of a bright or other color in the material indicates that the operator has forgotten the vital sterilization or disinfection step.

As shown in FIG. 17, the color change may also occur in another embodiment where the photochromic dye is incorporated into the device 10 through addition of the dye to the polymer making the body 12 and/or septum 16. The preferred housing polymer is polycarbonate but may be other clear or translucent polymers such as acrylic, polyvinylchloride, polypropylene, and polyurethane. The addition of the dye may occur at the time the polymer is polymerized or during a subsequent compounding operation. The dye may also be added at the time of injection molding of the body 12 or septum 16.

In another embodiment, the photochromic dye may also be applied as a coating to the body 12 or septum 16. The dye may be mixed with a solvent and the mixture sprayed, poured, atomized, printed, or dipped onto the appropriate surface. The solvent will evaporate leaving the dye on the surface. The photochromic dye may also be printed onto a label and the label attached to the device 10.

Figure 18:
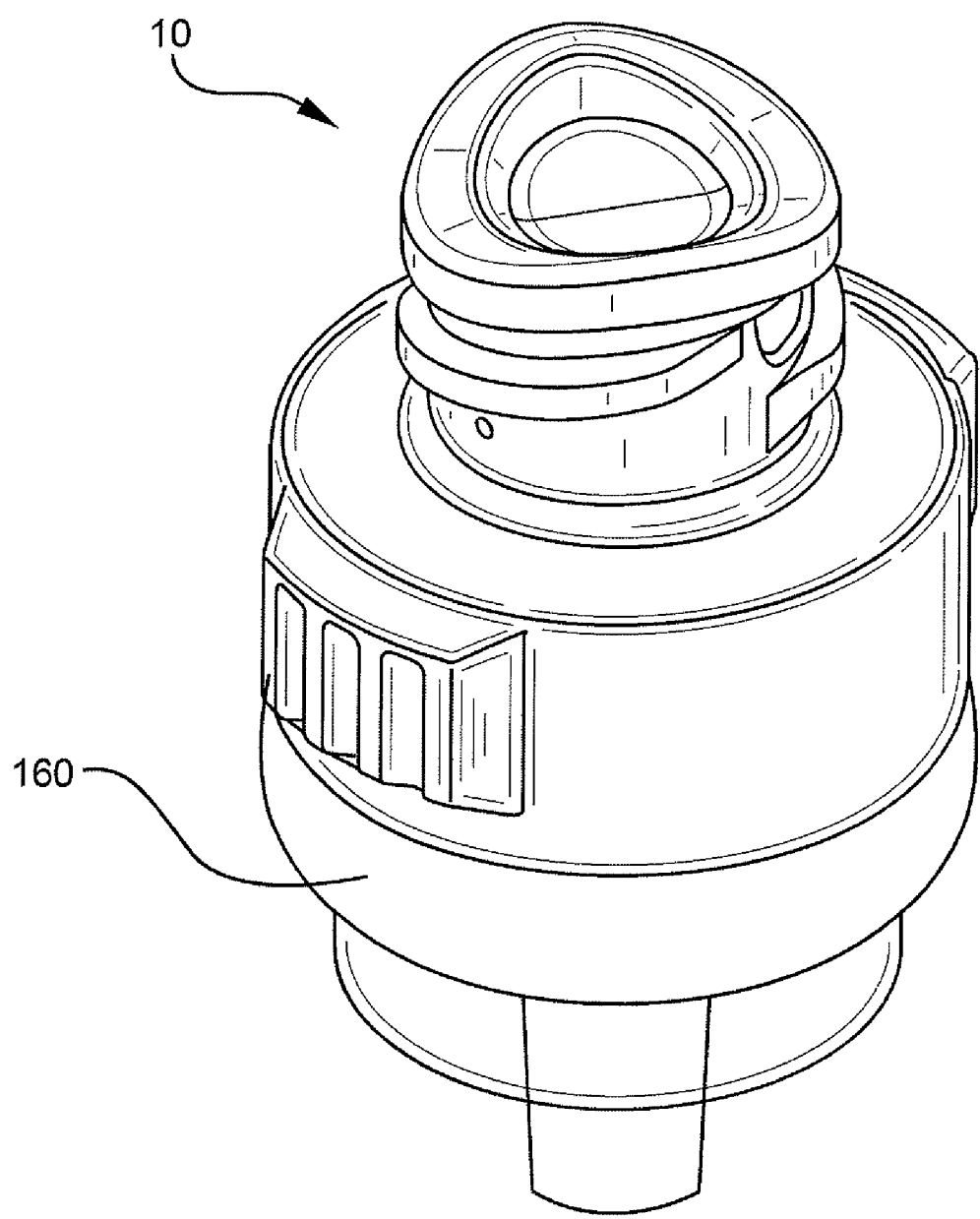
FIG. 18 is a perspective view of a lightened photochromic disk as a status indicator attached to a vascular access device.
Figure 19:
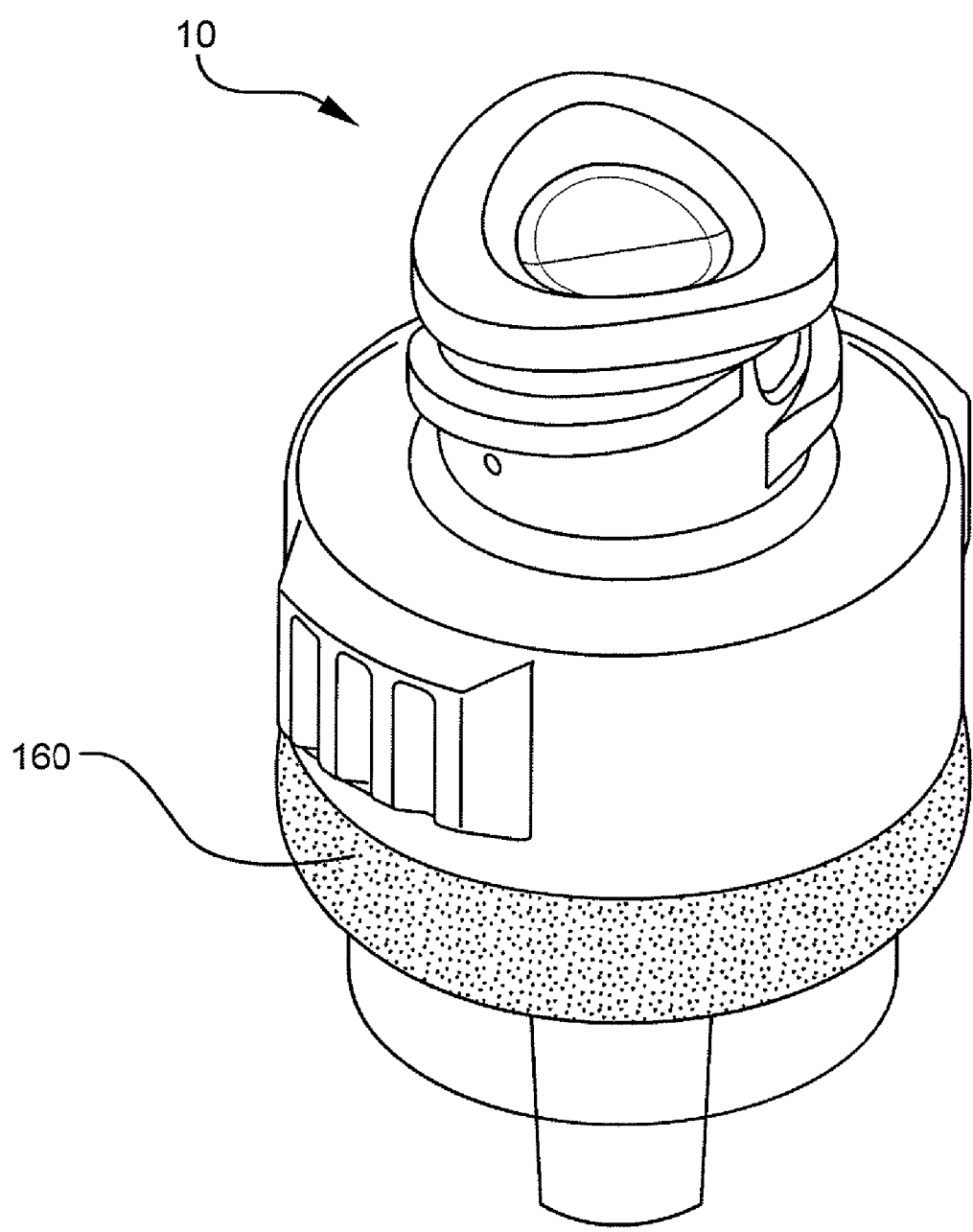
FIG. 19 is a perspective view of a darkened photochromic disk as a status indicator attached to a vascular access device.

Referring now to FIG. 18, a disk 160, as previously discussed, is attached to the exterior surface of the device 10. Referring now to FIG. 19, the disk 160 has changed from a light color to a dark color consistent with the principles discussed herein.

In another embodiment, a status indicator may communicate an elapsed period of time to an operator through a transparency or refractive index change of a material forming the body 12 of the device 10. The change of transparency of the substrate of the material may be initiated by oxidation, moisture absorption, or polymer crystallization. In this embodiment, the substrate includes a compound that is sensitive to oxidation, and when oxidized, changes the substrate's refractive index. In another embodiment, the substrate is a material that absorbs moisture. When the moisture content of the substrate reaches a specified amount, the substrate swells, causing a change in optical properties of the material. In another embodiment, a substrate polymer may crystallize, causing an optical change such as a change in clarity of the material. In the embodiments above, the substrate may form the body 12 of the device 10, may be a separate disk as shown in FIGS. 18 and 19, or may be a label as shown in FIG. 20.

Figure 21:
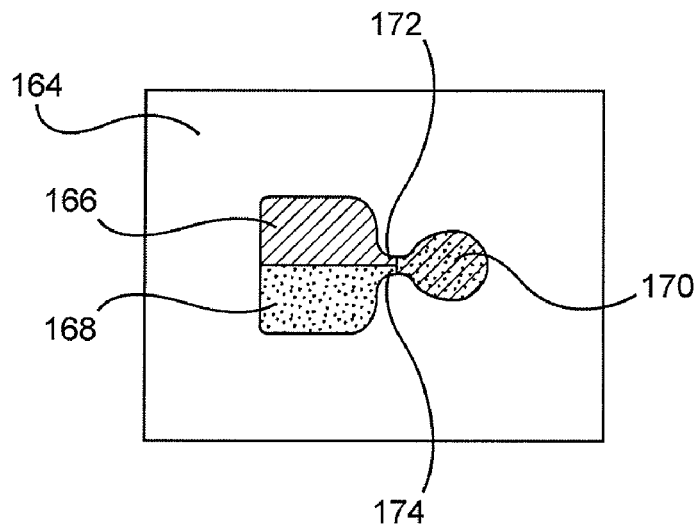
FIG. 21 is a side view of a label with multiple chemical reservoirs as a status indicator.

Referring now to FIG. 21, a status indicator 164 is a label that may be attached to a device 10. The label includes a first chemical 166 and a second chemical 168. The chemicals 166 and 168 are contained in separate reservoirs that are obscured from view of an operator via a mask of the multi-layer label 164. The status indicator 164 is activated by compressing the reservoirs using either an operator's fingers or an action that is performed in conjunction with installation, cleaning, attachment of the device 10 to another device, or other use of the device 10. Upon activation, the two chemicals 166 and 168 are mixed in a chamber 170. Upon mixing, the chemicals react with each other and change colors. The chamber 170 is viewable to an operator. When the operator sees a change of color in the window of the chamber 170, the operator will know that a predetermined amount of time has elapsed. The two chemicals 166 and 168 may travel from their separate reservoirs into the chamber 170 by means of a porous or absorbent material or by means of micro fluid channels 172 and 174. In another embodiment, a change of pH when the two chemicals 166 and 168 are mixed results in a color change within the chamber 170. In another embodiment, the reservoirs containing the chemicals 166 and 168 are separated from each other and/or from the chamber 170 using a breakable seal similar to seal 132 described earlier with reference to FIG. 12.

In another embodiment, a device 10 package is resistant to the environmental factors that initiate a time sequence of any of the status indicators discussed herein. Depending on the particular status indicator, the package includes a barrier to light, oxygen and/or other gasses, and moisture, as appropriate. The package may also include a mechanism to initiate the time sequence of the particular status indicator upon removal from the package.

The status indicator time sensitive signals, discussed above, that are communicated to an operator, correlate with the risk level that has been shown to result in catheter related blood stream infections (CRBSIs) if exceeded. The activation time for the signal may be different, depending upon device 10 application. As stated previously, the risk of contamination and pathogen colonization increases with device 10 usage. For devices used in a high use application such as an intensive care unit (ICU), a short (24 hours) time sensitive status indicator will be used. For medium use applications, the activation time may be 48 hours. And, for minimal use applications the signal activation time may be 72 hours to 96 hours, or greater.

Figure 22:
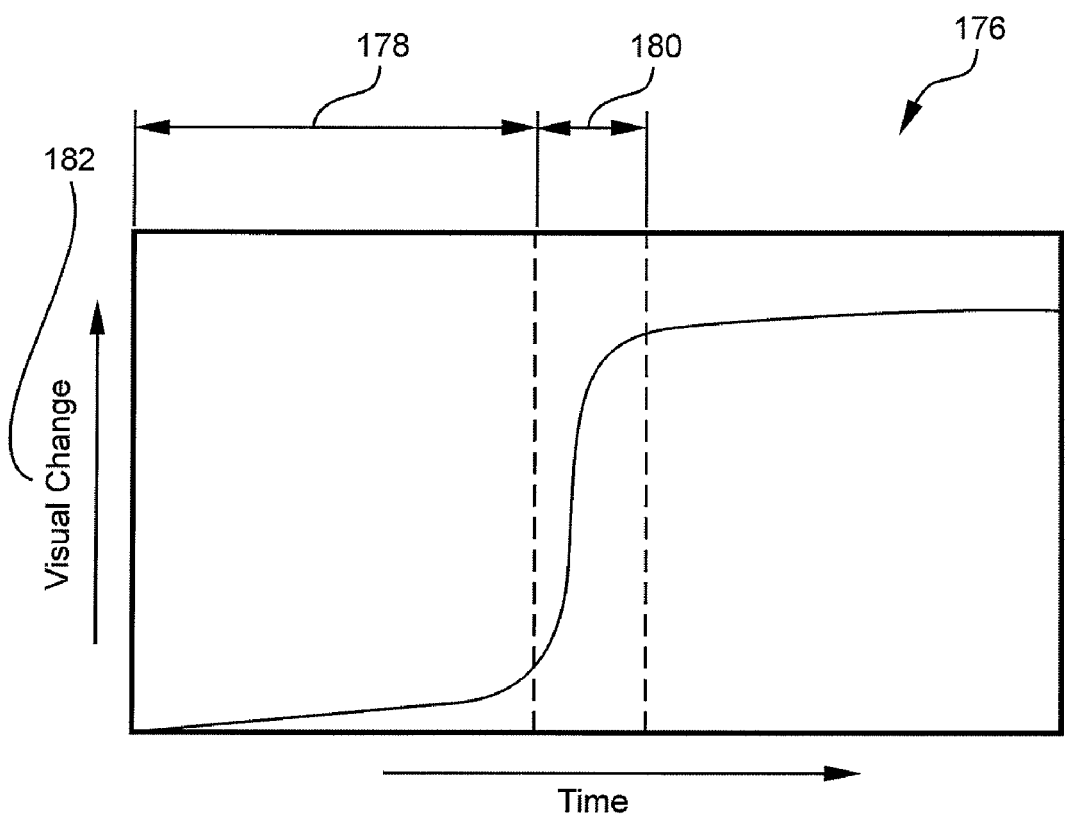
FIG. 22 is a timing diagram of the visual change of a status indicator.

Referring now to FIG. 22, as discussed above, a status indicator may be a color change or may be a change of other visual properties, such as transparency. In one embodiment, the visual change timing will follow an s-shaped curve 176. As shown in FIG. 22, there will be no, or minimal, change for a specified period of time 178, and then the visual change will be quick, intense, and non-reversible for a separate period of time 180. The activation of the visual change 182 may be delayed to the desired time frames discussed herein. Initiation of the time sensitive status indicator may occur by exposing the status indicator to environmental factors such as light, air, and moisture as discussed herein. Initiation may also occur upon removing the device 10 from its sterile package, initial usage or actuation of the device 10 through normal or deliberate use, or by manual or other actuation of the operator.

Figure 23:
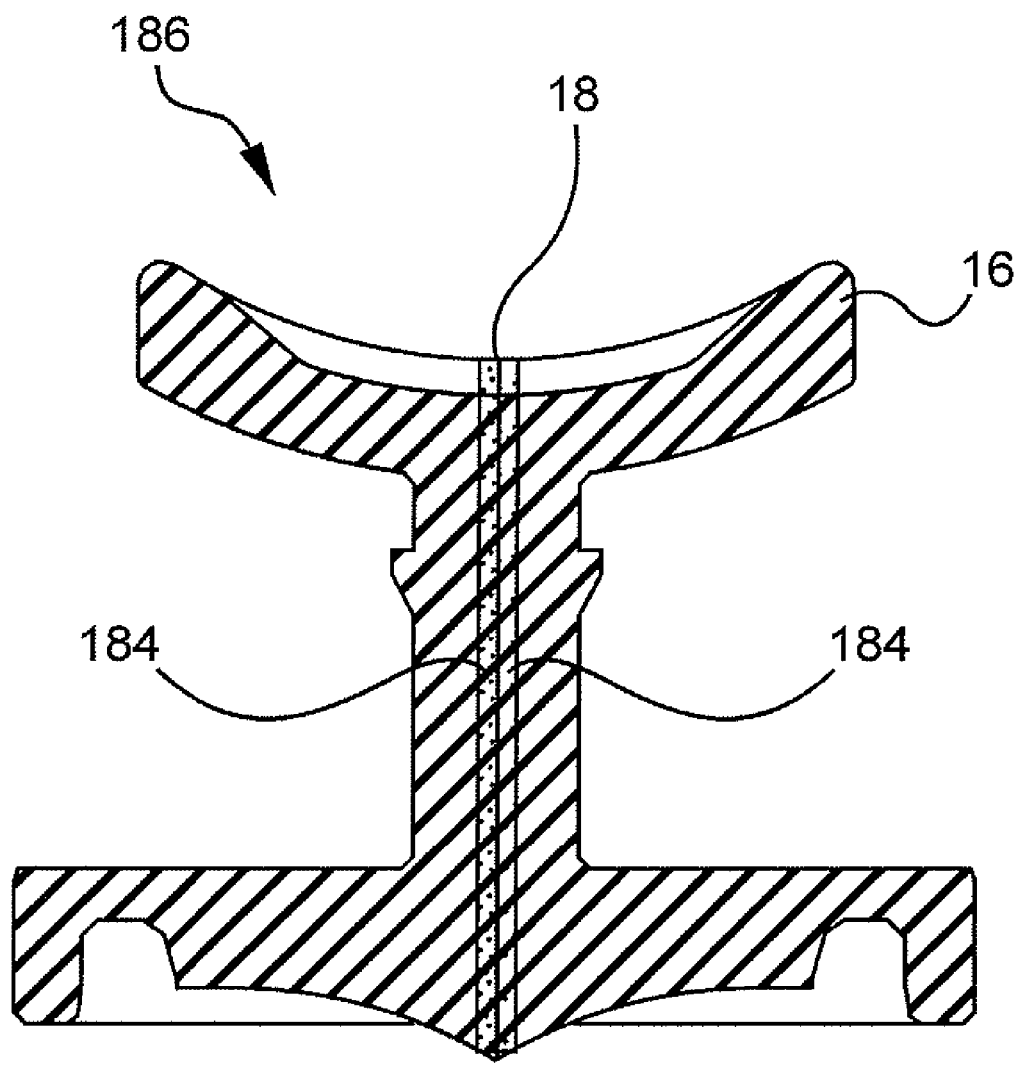
FIG. 23 is a cross section view of a status indicator on the slit of a septum.

Referring now to FIG. 23, the septum 16 of the vascular access device 10 of FIG. 1 is shown. The septum 16 includes a slit 18 through which a needle, catheter, or male Luer may be inserted into the device 10. The surface of the slit 18 may be coated with a lube or adhesive 184. The lube or adhesive 184 as shown in FIG. 23 is a cross-linking silicone lube that glues or otherwise adheres the slit 18 shut after a given amount of time. The silicone cross-linking of the silicone material that forms the body of the septum 16 can be initiated, initialized, or catalyzed by enzymes produced by a bacteria or other pathogen. After a period of time, the septum 16 of the device 10 is colonized by bacteria or other pathogen, and the slit 18 is glued shut by the lube 184, thus blocking access of a needle, catheter, male Luer, or other device that an operator may desire to insert through the septum 16. Thus, in the embodiment of FIG. 23, a status indicator 186 is a mechanical indicator that prevents an operator from further accessing the septum 16 after a predetermined amount of time. The type and amount of adhesive or lube 184 that is used and the location at which the lube or adhesive 184 is applied along the length of the slit 18 may be varied to adjust the speed or rate at which the slit is sealed.

Alternatively, the adhesive may be time sensitive due to moisture sensitivity. The adhesive gradually absorbs moisture over a predetermined period of time. Once moisture is absorbed to a specific level the slit 18 may be glued shut as discussed above.

In addition to the embodiments discussed above with reference to FIGS. 1 through 23, a status indicator can indicate an amount of use by an operator in addition to or in place of an elapsed period of time. Embodiments of status indicators which can communicate usage of a device 10 to an operator are discussed with reference to the following figures.

Figure 24:
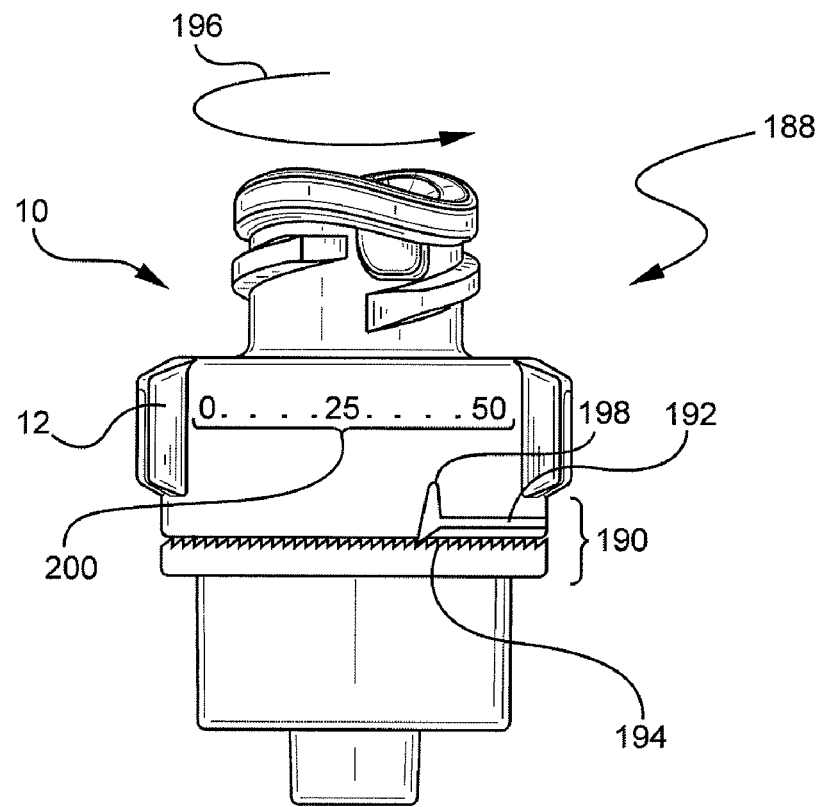
FIG. 24 is a side view of a ratchet status indicator of a vascular access device.

Referring now to FIG. 24, a status indicator 188 provides an indication of usage of a vascular access device 10. The status indicator 188 includes a ratcheting mechanism 190 that includes a ratchet 192 that communicates with multiple sequential teeth 194 of the ratcheting mechanism 190. As the ratchet 192 articulates between the multiple sequential teeth 194, the ratchet 192 is advanced from a first position to a second position in a direction 196 along the device 10.

Figure 25:
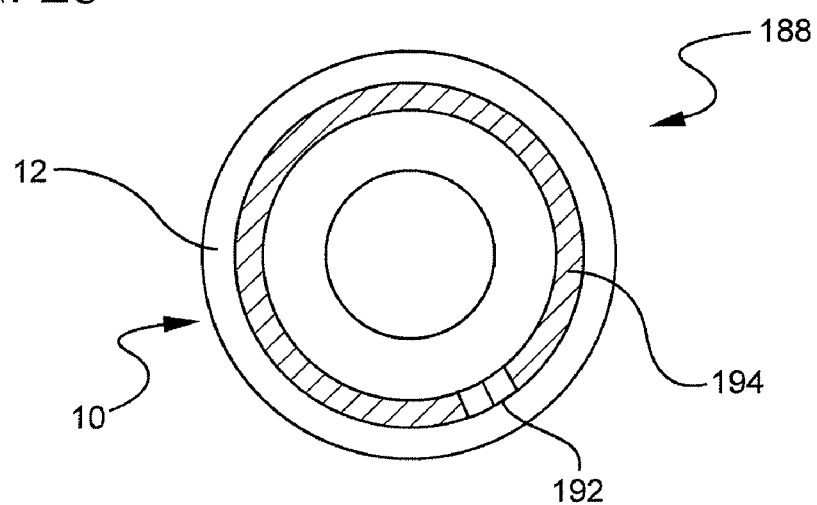
FIG. 25 is a top view of the ratchet status indicator of FIG. 24.

Referring now to FIG. 25, a top view of the status indicator 188 is shown. The device 10 is often accessed by another device from a direction shown in the view of FIG. 25. When another device, such as a needle, catheter, or male Luer, accesses the device 10, the ratchet 192, which is spring loaded, is moved from a first elevation to a second elevation and articulated from a first tooth 194 to a second tooth 194 causing the ratcheting mechanism 190 to rotate the pointer 198 of the ratchet 192 to move along in a direction 196 as shown in FIG. 24. Thus, the ratcheting mechanism 190 may be used to sense an amount of usage of the device 10 as it is mated, combined, or otherwise accessed by other devices. Each time a device accesses device 10, the pointer 198 of the ratchet 192 will advance in a direction 196 to indicate that the device 10 has been accessed again. As shown in FIG. 24, a counter 200 illustrates to an operator the number of times the device 10 has been accessed by an operator. By viewing the counter 200 and the location of the pointer 198 in relation to the counter 200, any operator viewing the device 10 can understand the history of the usage of the device 10 without ever having seen the device or interacted with the patient during the life of the device. The status indicator 188 and ratcheting mechanism 190 of FIGS. 24 and 25 functions very similarly to the clicking mechanism of a pen. Any similar mechanism capable of indicating the usage of the device 10, including the ratcheting mechanism of a pen, may come within the scope of the status indicator 188 as described herein. The ratchet 192 and/or the pointer 198 may be any size, shape or color and may become visible in any window, or series of windows, or may be visible along the entire body 12 of the device 10.

Figure 26:
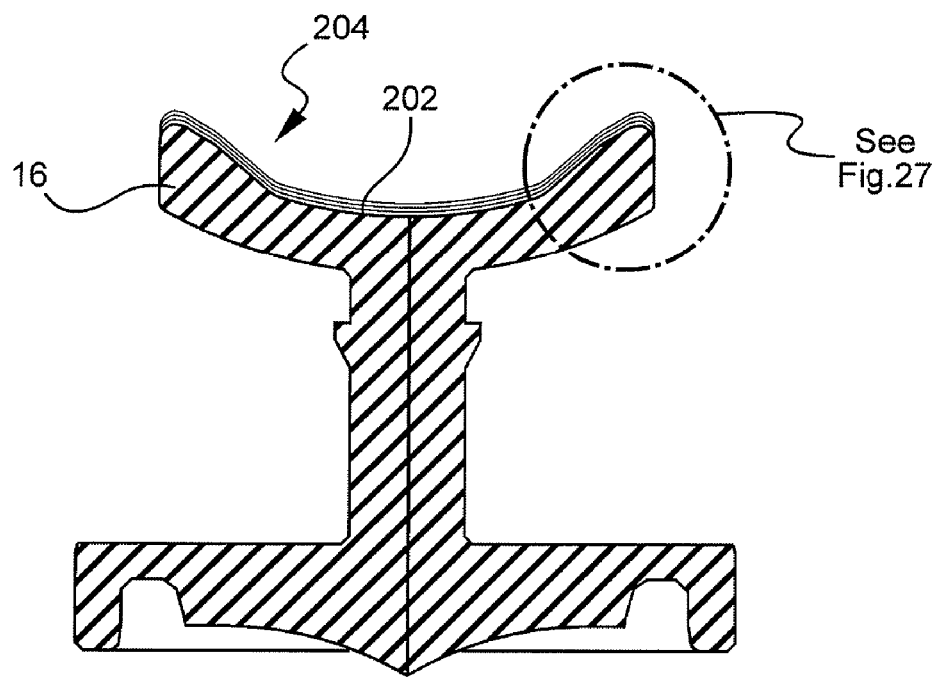
FIG. 26 is a cross section view of a multi-layered status indicator.

Referring now to FIG. 26, a septum 16 of a vascular access device 10 includes a status indicator 204 on the top external surface 202 of the septum 16. The status indicator 204 includes at least one removable layer of colored material on the external surface 202 of the septum 16.

Figure 27:
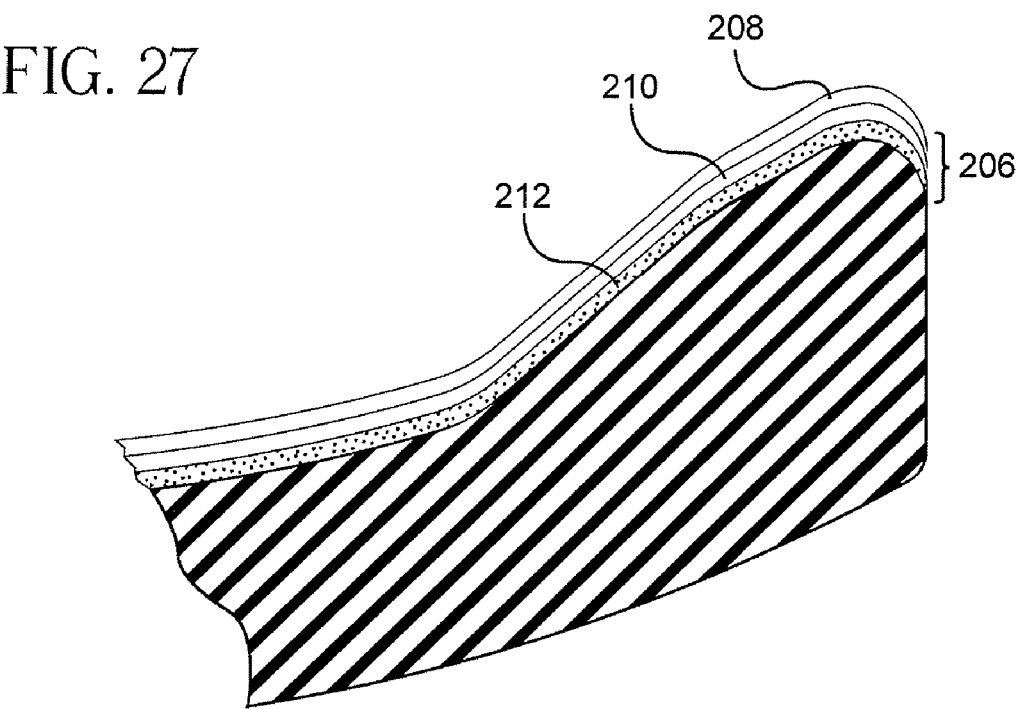
FIG. 27 is a close up cross section view of the multi-layered status indicator of FIG. 26.

Referring now to FIG. 27, an exploded cross-section view of the status indicator 204 of the septum 16 of FIG. 26 is shown. The status indicator 204 includes multiple layers 206 of different colored materials. A first layer 208 is colored green, a second layer 210 is colored yellow, and a third layer 212 is colored red.

Figure 28:
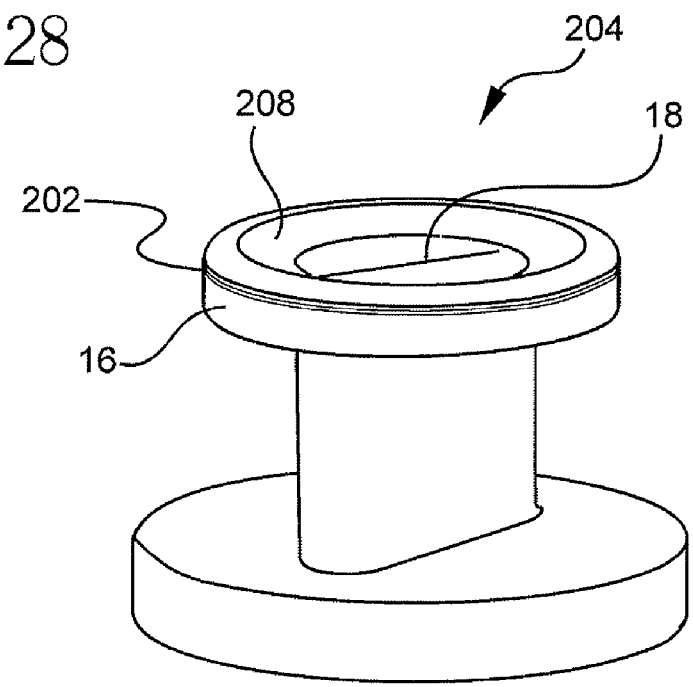
FIG. 28 is a perspective view of the top of a septum having a multi-layered status indicator.

Referring now to FIG. 28, initially, the surface 202 of the septum 16 is coated with all three layers of soft and easily abraded colored material. The material may also be slightly alcohol soluble. Thus, the status indicator 204 of FIG. 28, shows a top green layer 208 of material at its most external surface.

Figure 29:
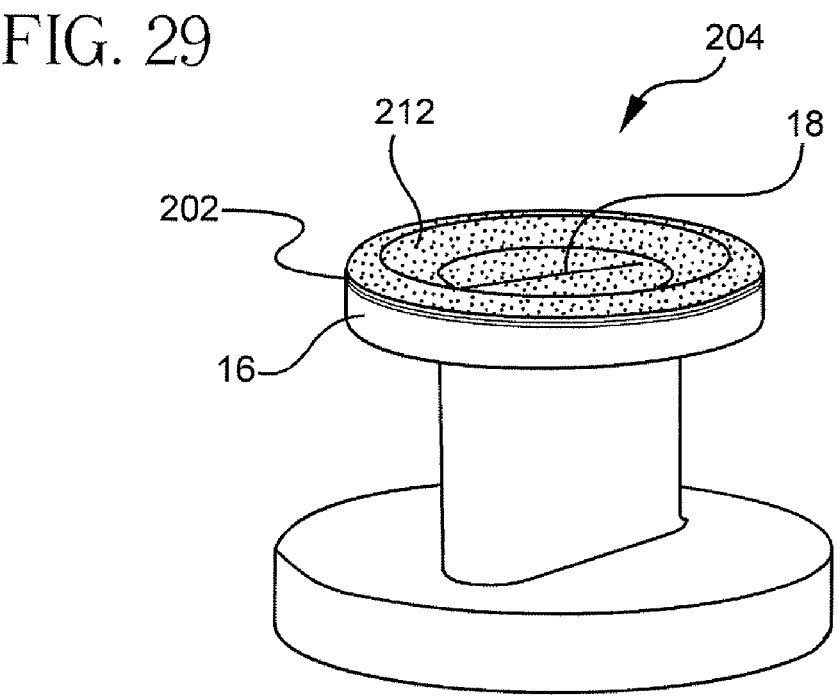
FIG. 29 is a perspective view of the top of a septum having a multi-layered status indicator after use.

Referring now to FIG. 29, after an operator abrades, actuates, swabs, or otherwise disturbs the top surface 202 of the septum 16, the top green layer 208 will be removed and the middle yellow layer 210 will be exposed. After further access and use of the device 10, the yellow layer 210 will be removed, exposing the red bottom layer 212. When any or all of the top surface 202 is shown as a red 212 color to the operator, the operator will know that the device 10 has received a certain amount of usage. The operator may then choose to clean and/or replace the device 10.

In one embodiment, the status indicator 204 of FIGS. 26 through 29 includes a material that is soluble to alcohol. Operators often swab alcohol on the exterior surface 202 of the septum 16 in order to clean the device 10 and kill any bacteria or other pathogens that are on the surface 202 of the septum 16 or within the slit 18 of the septum 16. By allowing the layered material to be slightly alcohol soluble, the material can change color, texture, and/or shape in order to visually communicate to an operator that the device 10 has been swabbed one or more times. In another embodiment, the material may be an easily abraded colored material which when touched, swabbed, or otherwise accessed or disturbed, changes color or shape. In another embodiment, multiple layers 206 having multiple characteristics including alcohol solubility, saline solubility, water solubility, and abrasion, may be stacked upon each other to achieve a variety of affects in order to tailor the septum 16 and the status indicator 204 to a particular use within a hospital.

Figure 30:
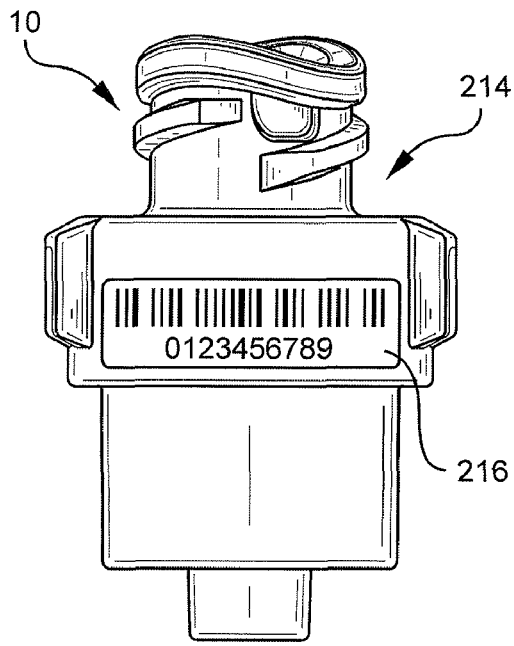
FIG. 30 is a side view of a bar code status indicator of a vascular access device.

Referring now to FIG. 30, a status indicator 214 includes a bar code label 216 secured to a vascular access device 10. When the device 10 is put into service, and each time the device 10 is accessed, an operator scans the bar code 216 with a bar code scanner to keep track of the time the device 10 is in use and the number of times the device 10 has been accessed. A database within the bar code scanner or other device capable of receiving data from the bar code scanner provides an alarm when either time or access limits are reached. For example, after 24 hours after the device 10 was initially scanned in a first time, a device may provide an alarm to the operator which indicates that the device 10 has been in use for at least 24 hours. Alternately or additionally, an alarm which indicates that a maximum number of accesses has been reached may also be communicated to an operator. The bar code 216 may come in the form of a label or hang tag or other structure that it is attached, affixed, or otherwise secured or connected to the device 10.

Figure 31:
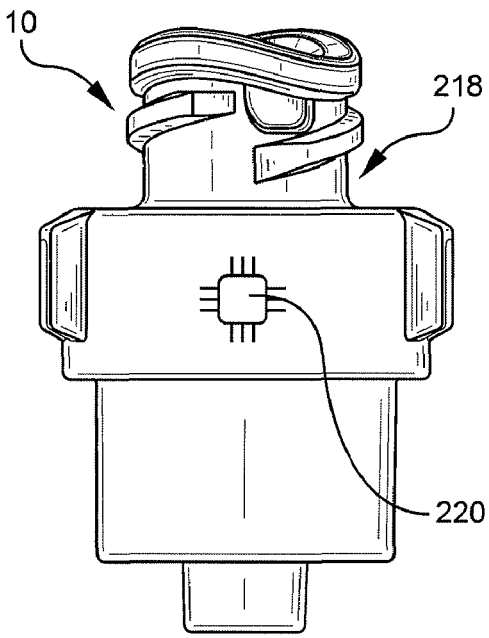
FIG. 31 is a side view of a radio frequency identification chip status indicator of a vascular access device.

Referring now to FIG. 31, a status indicator 218 includes a radio frequency identification (RFID) chip 220. The RFID chip 220 is placed on the external surface of a vascular access device 10. The RFID chip 220 permits the device 10 to store information relative to the amount of time the device 10 has been in service and/or the number and frequency of accesses or uses of the device 10. A scanner is used to signal the chip 220 when the device 10 is put into service, and each time the chip 220 is accessed, so that the chip 220 can record the data. The scanner can also read the start time and the number of accesses from the chip 220. Thus, the embodiment of FIG. 31 of a status indicator 218 provides an advantage over the status indicator 214 of FIG. 30, because the information is stored in the chip 220 of the device 10 and not in remote database of a bar code scanner or other device. A number of different scanners can access and manipulate the information on the device 10 without requiring a single scanner to follow the device 10 or without requiring a link to a central remote database. Thus, each of a number of different operators who come into contact with the device 10 may have their own separate scanner and can learn about the history of the device 10 independently.

Figure 32:
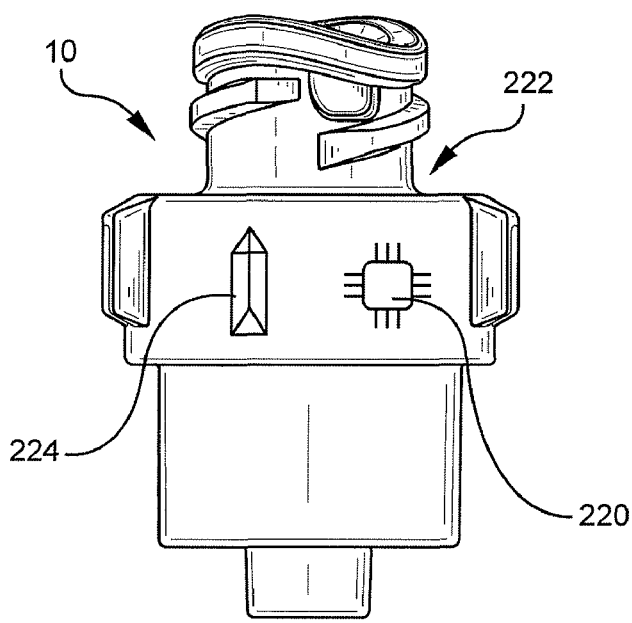
FIG. 32 is a side view of a piezoelectric crystal status indicator of a vascular access device.

Referring now to FIG. 32, a status indicator 222 includes a piezoelectric crystal 224 in series with an RFID chip 220. The piezoelectric crystal 224 senses when the device 10 is activated and produces a small amount of electrical charge when the crystal is compressed by use of the device 10. The charge produced by the crystal 224 is detected by the RFID chip 220, and the RFID chip increments the counter based on the number of accesses or uses. Thus, the embodiment of the status indicator 222 of FIG. 32 does not require a separate scanner to indicate whether or not the device 10 has been used. Rather, the RFID chip 220 senses each use of the device 10 upon compression of the device by the handling of an operator. A scanner is only required to be used in order to retrieve the collected information of the RFID chip 220. Various other circuits and electrical components in addition to those illustrated in FIGS. 30 through 32 are possible.

In addition to the multiple embodiments discussed herein directed to detecting the time and usage of a device 10, other embodiments of status indicators described herein can provide an indication of disinfection, sterility, cleanliness, or the presence or absence of a bacteria or other pathogen in or on a device 10.

Figure 33:
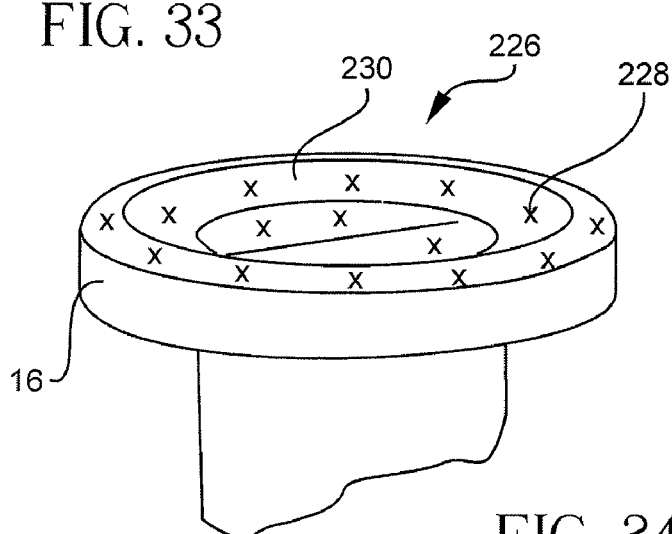
FIG. 33 is a perspective view of a thermochromic status indicator layer on the top of a septum.

Referring now to FIG. 33, a status indicator 226 includes a thermochromic material 228 on an external, swabbable surface 230 of a septum 16 of a vascular access device 10. The thermochromic material 228 is applied as a coating on the septum 16. In another embodiment, the material 228 is applied as a compound into the material of the septum 16 itself. The thermochromic material 228 is a status indicator 226 that provides a reversible indication of cleaning and disinfecting. Upon swabbing the surface 230 with alcohol or another rapidly evaporating liquid, the surface 230 changes color temporarily to another color indicating that the device 10 has been cleaned. After accessing the device 10, and after the alcohol or other liquid is fully evaporated, the color of the thermochromic material 228 will change to its original color.

The color change may be accomplished via thermochromism which is the ability of a substance to change color due to a change in temperature. Two thermochromic approaches are based upon liquid crystals and leuco dyes. Liquid crystals are capable of displaying different colors at different temperatures. The crystalline structure of the material changes as the temperature changes resulting in selective reflection of certain wavelengths. The crystals will assume the original structure upon return of temperature to the starting point. Therefore, the color of thermochromic liquid crystals is changeable and reversible. Liquid crystals may be encapsulated in microcapsules.

A leuco dye is a dye whose molecules can acquire two forms, one of which is colorless. For example, the spiro form of an oxazine part of the molecule is separated by a $SP^3$-hybridized, or spiro, carbon. An illustrative example includes microcapsules with crystal violet lactone, weak acid, and a dissociable salt dissolved in dodecanol are encapsulated. When the solvent melts, the salt dissociates, the pH inside the microcapsule lowers, the dye becomes protonated, its lactone ring opens, and its absorption spectrum shifts drastically causing the dye to become deeply violet.

Another thermochromic material is polythiophene. Chains of a polyacrylamide derivative are attached to a polythiophene backbone. At lower temperatures the chains are irregular and stretched out. As the temperature is increased the chains and backbone pull into a compact spherical structure. This conformational change causes a color change of orange-red to yellow.

As shown in FIG. 33, in use, an operator prepares to access the device 10 by swabbing the top surface of the septum 16 with an alcohol wipe or similar disinfecting tool. Following swabbing, the alcohol applied to the surface 230 begins to evaporate. As the alcohol evaporates, the surface temperature decreases, causing the thermochromic material 228 to change color. The color change may be a status indicator 226 to the operator that the septum 16 disinfected and the device 10 is ready for access. As the temperature of the septum surface returns to room temperature, the color change reverses, returning to the original color or no color.

70% isopropyl alcohol evaporating from a stainless steel surface may cause a temperature shift of 20 degrees F. The septum 16 and coating may be made from a polymer. However, polymers do not have good thermal conductivity. Therefore, the temperature change caused by the evaporation of alcohol from a polymer surface may not be as large as that from stainless steel. Thus, metal nanoparticles may be added to the septum 16 material or coating to improve thermal conductivity.

Figure 34:
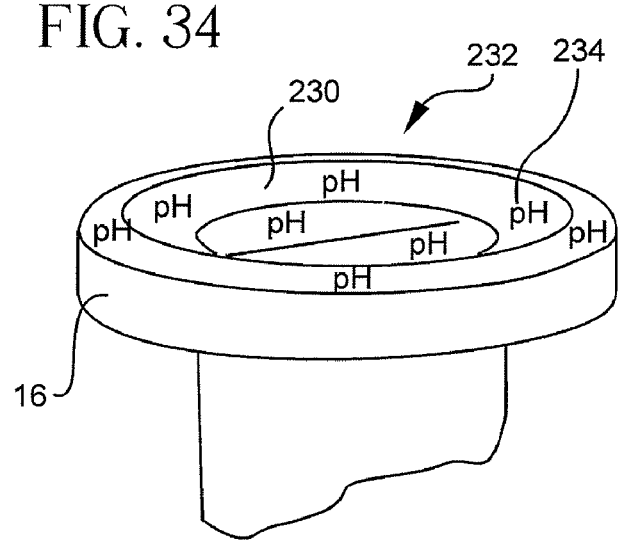
FIG. 34 is a perspective view of a pH sensor status indicator layer on the top of a septum.

Referring now to FIG. 34, a status indicator 232 includes at least one pH sensor 234. The pH sensor 234 is located on the exterior surface 230 of the septum 16 of a device 10. The pH shift can indicate whether or not the septum 16 has been swabbed with a substance containing a pH within a specific range. The pH of 70% isopropyl alcohol in water is between five and six. A reversible pH sensor 234 sensitive to a pH range of five to six is integrated into the swabbing surface 230 by a coating or by compounding the sensor 234 into the material of the septum 16. Upon swabbing the surface 230, the alcohol solution causes the pH sensor 234 to change colors indicating that the device 10 has been disinfected and is ready for access. Following evaporation of the alcohol solution, the pH of the swabbing surface 230 will shift outside the sensor range of five to six, and the sensor 234 will return to a baseline color.

Figure 35:
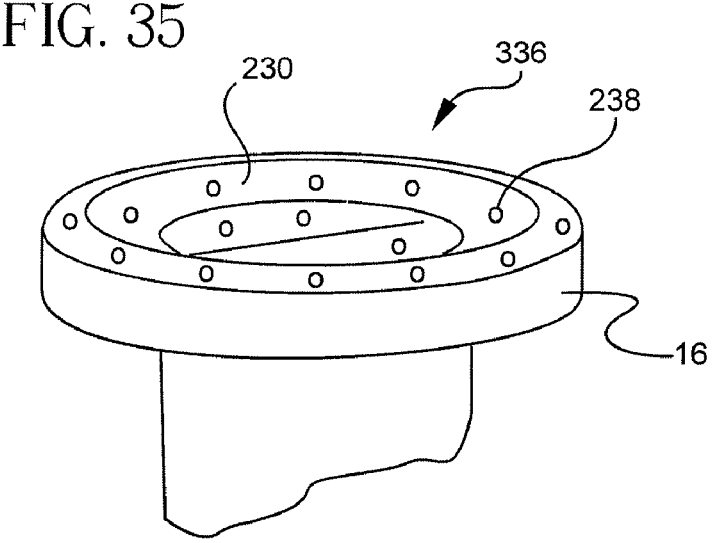
FIG. 35 is a perspective view of an alcohol sensor status indicator layer on the top of a septum.

Referring now to FIG. 35, a status indicator 236 includes an alcohol sensor 238 on the surface 230 of a septum 16 of a vascular access device 10. The alcohol sensor 238 initiates a color change caused by a chemical reaction between a chemochromic compound and alcohol solution or other disinfecting agent. The chemochromic compound of the alcohol sensor 238 may be integrated into the swabbing surface 230 via coating or may be compounded into the material of the septum 16 itself. Upon swabbing the surface 230 with alcohol, the alcohol solution reacts with the chemochromic compound, causing a color change and indicating that the device 10 has been disinfected and is ready for access. Following evaporation of the alcohol solution, the reaction would reverse and the chemochromic compound of the sensor 238 would return to a baseline color. An alcohol indicator consisting of a carrier matrix with an alcohol oxidase enzyme which catalyzes a reaction converting alcohol to an oxidizing agent, and a hydrogen donor indicator which changes color when oxidized, may be used. Examples of hydrogen donors include 2,2'-azinodi-(3-ethylbenzthiazoline sulfonic acid); 3-methyl-2-benzothiazolinone hydrazone and 3-dimethylaminobenzoic acid; 3,4-dichlorophenol and 4-aminophenazone, o-tolidine; and o-tolidine and dianisidine.

Several other additional or alternative chemicals may be identified or developed to exhibit a reversible or irreversible color change when exposed to alcohol, chlorhexadine gluconate (CHG), or other common disinfectants. Several companies currently produce test strips that react to the alcohol that is present in saliva after alcohol has been consumed. One such strip is produced by Chematics and is named the ALCO-SCREEN™ test strip. The ALCO-SCREEN™ test strip will turn green or blue when exposed to saliva containing alcohol. With higher concentrations of alcohol than that found in saliva, the strip will turn, through a chemical reaction, to a dark brown or black color. Such a strip in another embodiment, may be applied to the surface of the septum 16 or any portion of the device 10.

Figure 36:
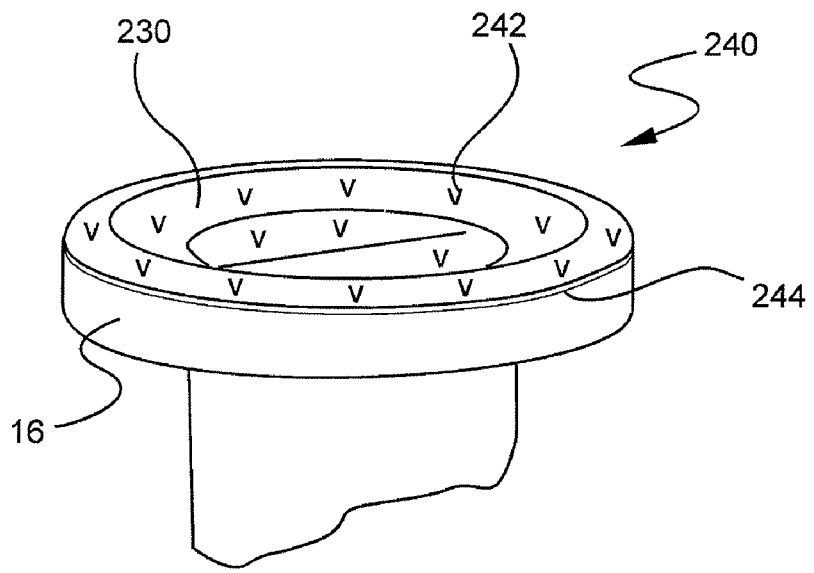
FIG. 36 is a perspective view of a textured surface status indicator layer on the top of a septum.

Referring now to FIG. 36, a status indicator 240 includes a textured surface 242 on the surface 230 of a septum 16. Beneath the textured surface 242, lies a colored substrate 244. When the textured surface 242 is swabbed with alcohol, water, or another disinfectant or liquid, the liquid is absorbed by the textured surface 242 and the contact surface 242 becomes nearly transparent. In its transparent state, surface 242 provides a window through which an operator may view the colored substrate 244. In this manner, a surface which is nearly frosted, opaque, or otherwise obscured when a surface finish is applied, becomes a transparent window to a more visible colored substrate when the surface is wetted. Thus, when the surface 242 is wetted, it will appear to take on the color of the submerged surface or colored substrate 244. After the liquid evaporates fully, the surface 242 will again appear frosted, opaque, or otherwise obscured.

Figure 37:
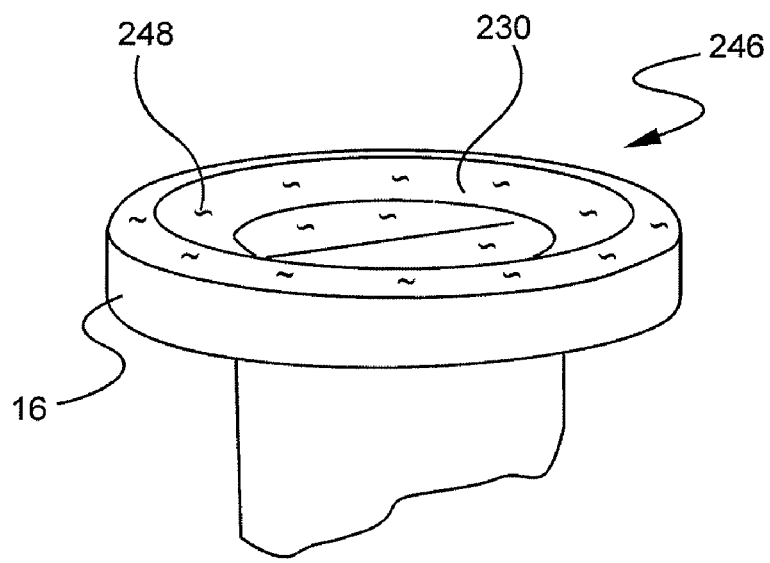
FIG. 37 is a perspective view of a moisture sensitive status indicator layer on the top of a septum.

Referring now to FIG. 37, a status indicator 246 includes a moisture sensitive layer 248 on the surface 230 of a septum 16. The moisture sensitive layer 248 may also be a moisture sensitive compound fully integrated with the material of the septum 16. Upon swabbing the surface of the moisture sensitive layer 248, the water of an alcohol solution may be absorbed by the moisture sensitive layer 248 causing a change in color and indicating that the device 10 has been disinfected and is ready for access. Following evaporation of the water of any liquid, the moisture sensitive layer 248 returns to a baseline color. Desiccants are an example of moisture sensitive layers or compounds. Many desiccants change to a blue color upon absorption of water and then return to a baseline color when the moisture is removed.

Figure 38:
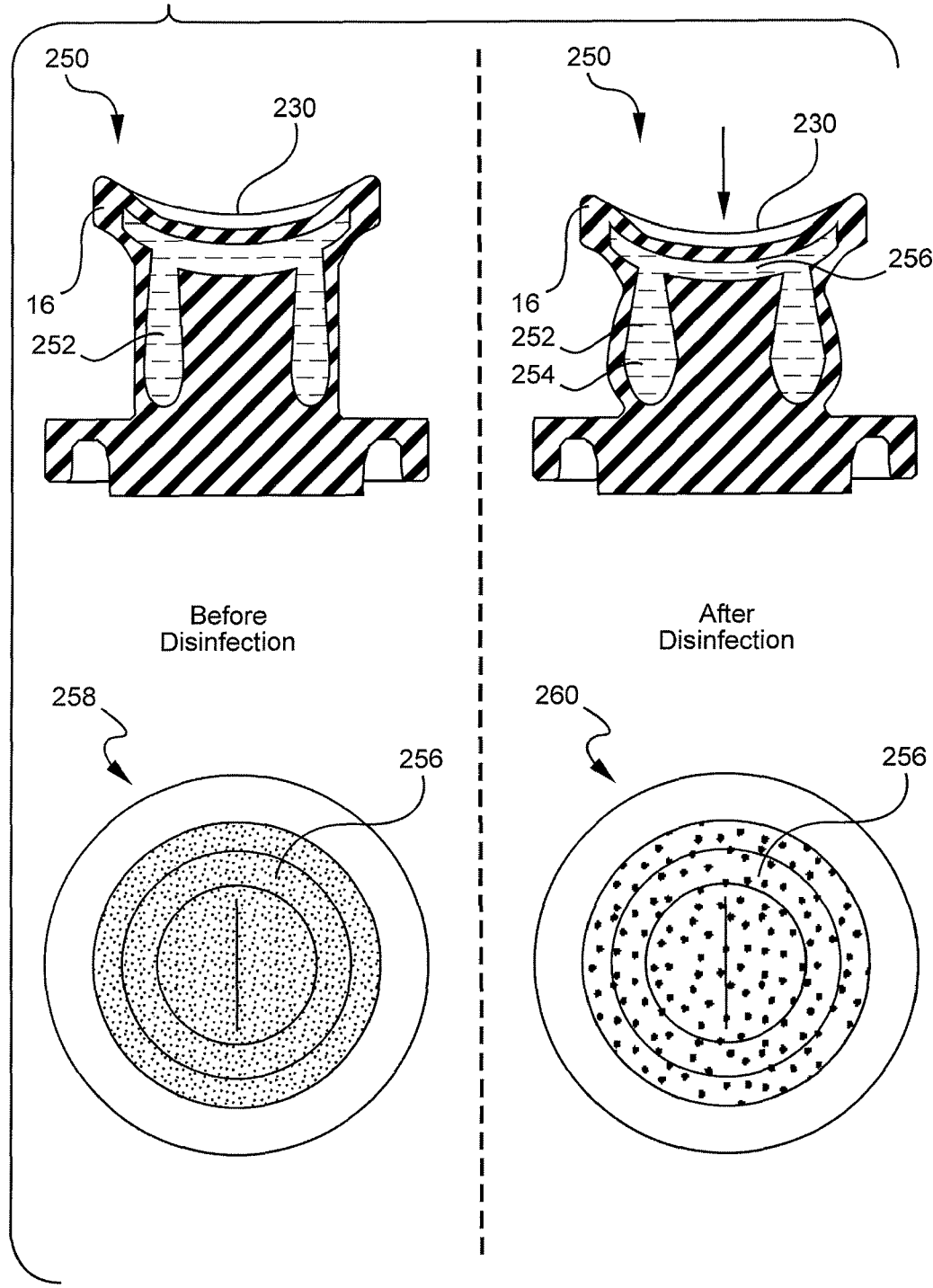
FIG. 38 is a cross section and top view of a dye transport reservoir status indicator before and after use.

Referring now to FIG. 38, a status indicator 250 includes a reservoir of colored liquid 252 with an elastomeric septum 16 of a vascular access device 10. The reservoir contains either an opaque white liquid or a colored dye. When properly designed, the reservoir is partially or fully evacuated when exposed to pressure on a surface 230 of the septum 16 during normal cleaning and use. The fluid 252 is then displaced into a storage reservoir under pressure. When the pressure is released, the fluid 252 will slowly flow back from the holding reservoir 254 into the original reservoir 256. FIG. 38 shows a top view 258 of the original reservoir 256 prior to use of the septum 16. The original reservoir 256 is shown in a dark color. After cleaning or use of the septum 16, a top view 260 shows the original reservoir 256 evacuated of the colored dye 252, thus leaving the original reservoir 256 as a lighter color than the original reservoir 256 of top view 258.

As shown in FIG. 38, the device 10 has a surface 230 that changes color when exposed to temperature change, alcohol, or other disinfectant. The device 10 then changes color back to the original color after an appropriate amount of time that would correspond to the time required for the disinfectant to evaporate and completely kill a bacteria or other pathogen. This would enforce two important behaviors for operators: first, proper and full disinfection, and second, waiting an appropriate amount of time before inserting a device into the septum 16. The rate at which the surface 230 is changed from a dark color to a light color may be adjusted by varying the type of liquid or other material placed within the reservoir, the size of the reservoir, the color of the material, and/or the dimensions and materials of the body of the septum 16.

Figure 39:
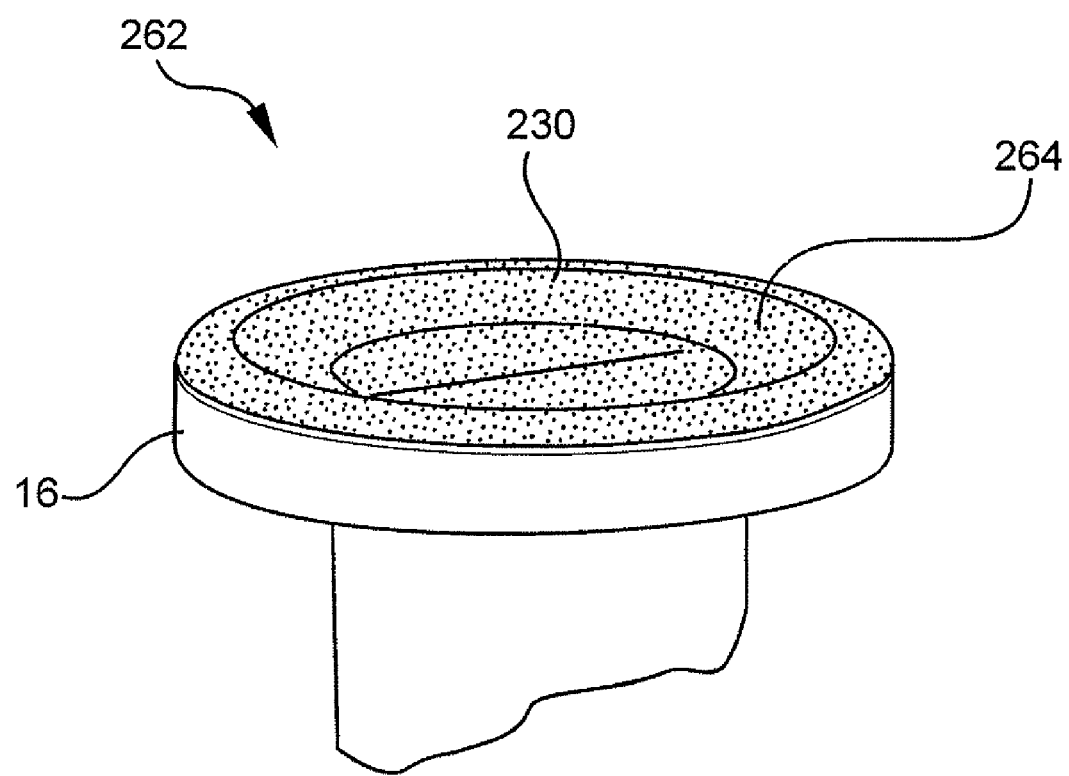
FIG. 39 is a perspective view of a piezochromic status indicator layer on the top of a septum.

Referring now to FIG. 39, a status indicator 262 includes a piezochromic material 264. The piezochromic material 264 is a material which will change color when exposed to pressure. The material 264 may be coated as a layer on a surface 230 of a septum 16. In another embodiment, the material 264 may be embedded into the surface of the septum. In yet another embodiment, the material 264 may be integrated into the material of the septum 16 as a compound. When proper disinfective swabbing occurs on the surface 230, the pressure caused from the swabbing action would cause the surface 230 to change color. As the pressure is removed, the surface 230 would return to its original color. This approach, like many other surface contact approaches described herein, encourages an operator to disinfect the entire surface of the corresponding status indicator.

Referring now to FIG. 40, a status indicator 263 includes a pathogen staining solution 265 or other reagent. The solution 265 is placed within a dual chamber syringe 266 containing both the solution 265 and a cleaning saline solution 268 divided by a movable stopper 270. The syringe 266 includes a plunger 272 and at least one notch 274 into which the movable stopper will collide as the plunger 272 is advanced through the lumen of the syringe 266.

Referring now to FIG. 41, the plunger 272 of FIG. 40 is shown advanced through the syringe 266 such that the movable stopper 270 has advanced and collided with the notches 274. In its advanced state, the plunger 272 has expelled the solution 265 into a vascular access device 10 and the leakage 276 caused by the collision of the movable stopper 270 with the notches 274 has permitted a saline solution 264 to leak past the movable stopper 270 and into the device 10.

An operator may attach the syringe 266 of FIGS. 40 and 41 to a device 10 and flush the syringe 266 as the operator would with any normal syringe. A main stopper 278 attached to the end of the plunger 272 pushes the saline 268, which pushes on the movable stopper 270, which in turn pushes the pathogen staining solution 265 into the device 10. The pathogen staining solution 265 stains all the microorganisms and pathogens as it passes them. When the staining solution 265 is fully flushed into the device 10, the movable stopper 270 reaches the notches 274 in the barrel of the syringe 266 allowing the saline 268 to leak past the movable stopper 270 and into the device 10. The saline 268 then flushes the staining solution 265 from the device 10 leaving the device 10 clear. Any microorganisms in the device 10 will now be stained and visible to an operator. In this manner, a device 10 and any other device to which the device 10 is attached may be checked for disinfection and the absence of pathogens each time the status indicator 263 is employed. As another embodiment, notches 274 may be supplemented or replaced by grooves or other recesses within the material of the barrel of the syringe 266. Fluid, such as saline 268, may flow through the grooves or recesses when the movable stopper 270 is in communication with the grooves or recesses.

Figure 42:
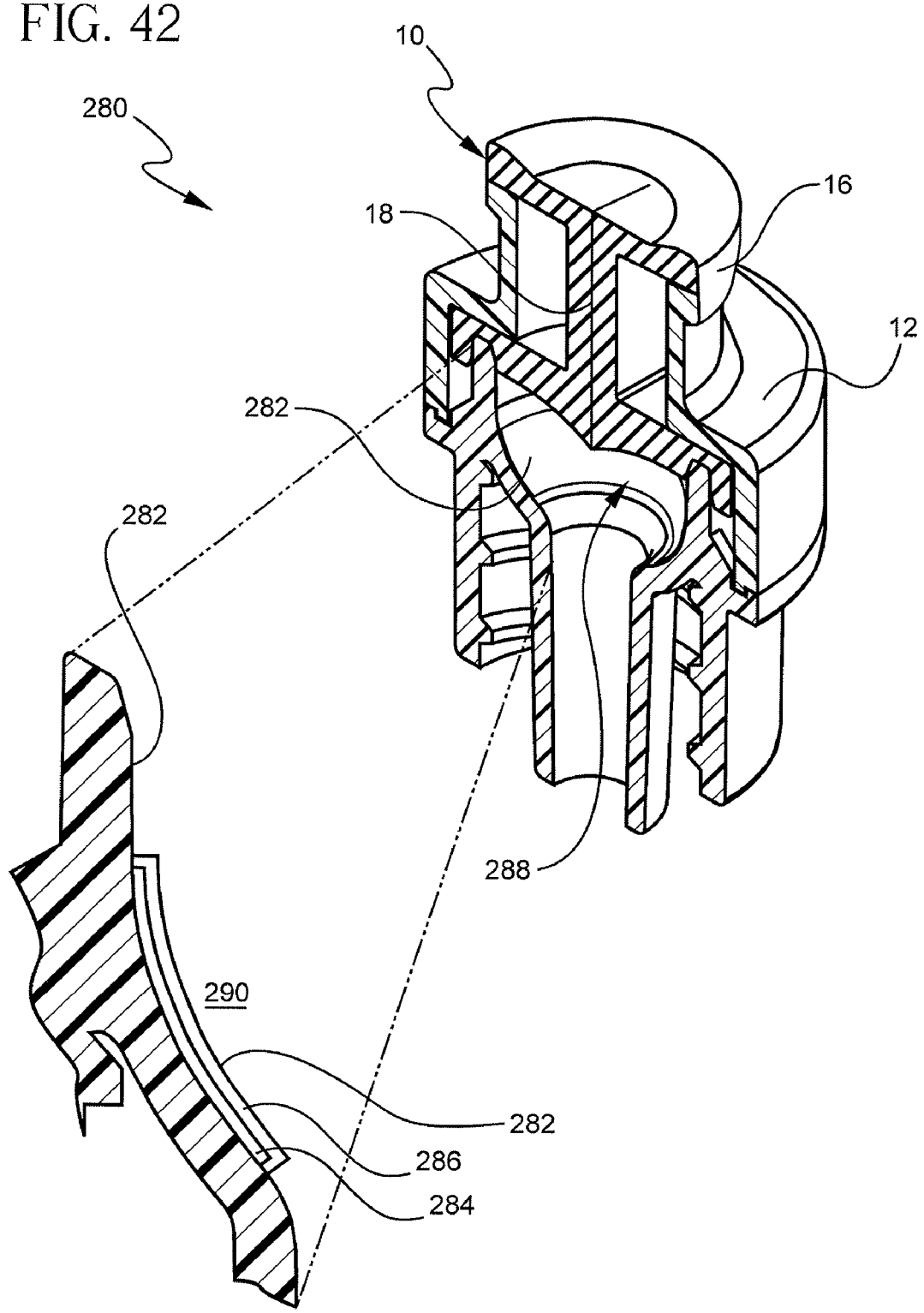
FIG. 42 is a cross section view and a close up cross section view of a status indicator of the inner surface of a vascular access device.

Referring now to FIG. 42, a close-up view shows a status indicator 280 disposed on the inner surface 282 of the body 12 of a vascular access device 10. The status indicator 280 includes a fluid activated dye 284 substrate beneath a degradable membrane 286. The chamber 288 within the device 10 fills with fluid 290 when the device 10 is placed in service. The fluid 290 in the chamber 288 comes into contact with the inner surface 282, causing the degradable membrane 286 to dissolve or degrade over a controlled period of time, thus exposing the fluid activated dye 284 to the fluid 290. When the fluid activated dye 284 changes color or otherwise causes the fluid 290 to change color, an operator will know that the device 10 has been exposed to fluid 290 and placed into service for a given period of time. The rate at which the degradable membrane 286 degrades or dissolves may be adjusted to produce the desired timing effect by varying the material properties, thickness, and location of application of the membrane 286 to the device 10.

In one embodiment, the status indicator 280 of FIG. 42 includes a color or other mechanism to alert an operator that the device 10 has expired. In another embodiment, the status indicator 280 of FIG. 42 includes a moisture sensitive layer or other fluid activated indicator in place of the fluid activated dye 284. When the moisture sensitive layer is exposed to the fluid 290, the layer will indicate to an operator that a given period of time has elapsed. In another embodiment, the status indicator 280 includes a lube or adhesive similar or identical to the lube or adhesive 184 discussed with reference to FIG. 23. In this embodiment, the lube or adhesive and the degradable membrane 286 are place on the exposed surface of the slit 18 of the septum 16. After the degradable membrane 286 is removed, the lube or adhesive will cause the slit 18 to seal, thus blocking further use and access of the device 10 to an operator.

In conjunction with any of the elements discussed here, further examples of status indicators may be provided. For example, a status indicator related to a label or other indicator capable of displaying a visual change over time may be provided in addition to, for example, the status indicators discussed with reference to FIGS. 13-22. Some of these examples of status indicators are discussed below.

Figure 43:
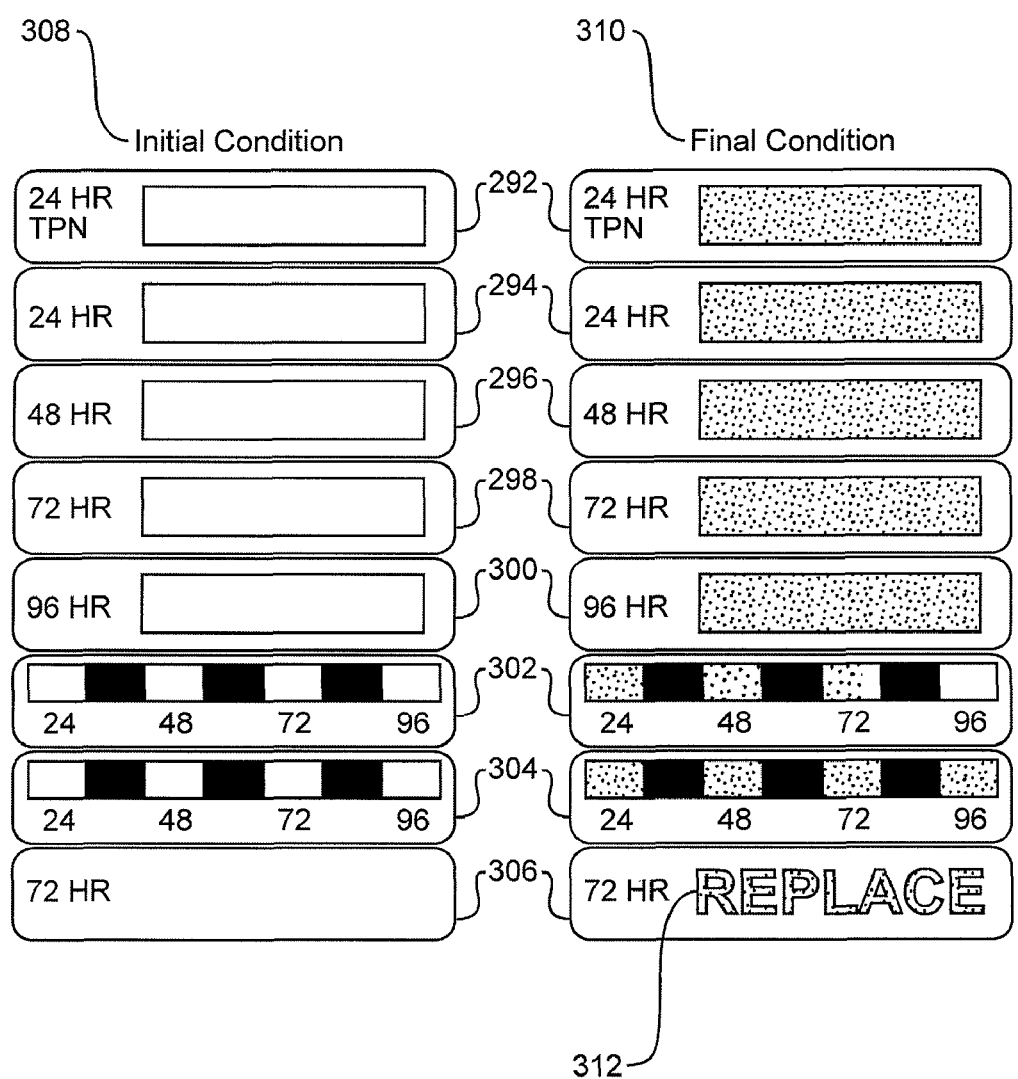
FIG. 43 is a front view of various status indicators in initial and final condition.

Referring now to FIG. 43, a device 10 may include at least one status indicator 292, 294, 296, 298, 300, 302, 304, and/or 306 in any combination. After an environmental, physical, temporal, or other change occurs, such as a change in light (using photochromic dyes or materials), oxygen level, temperature, use, cleaning, or time as previously discussed (for example, using dye migration that becomes visible over time), the status indicators 292, 294, 296, 298, 300, 302, 304, and/or 306 change from an initial condition 308 towards a final condition 310. In an initial condition 308, the status indicators 292, 294, 296, 298, 300, 302, 304, and/or 306 indicate that no significant change in environment, physical use, time, or other event has occurred.

For example, a temporal change (i.e., a change in time) may be recorded and displayed for a period of 24 hours as shown by status indicators 292 and 294, a period of 48 hours as shown by status indicator 296, a period of 72 hours as shown by status indicators 298 and 306, or a period of 96 hours as shown by status indicator 300. Any combination of multiple time periods may be recorded and displayed. For example, the status indicators 302 and 304 each record and display the multiple sequential time periods of 24, 48, 72, and 96 hours.

For temporal change, any time period may be measured as desired by a particular use, prescribed use, treatment regime, facility policy, industry guideline or recommendation, or as required by law. For example, 24 hours may be recorded and displayed on a label attached to a catheter or other tubing used for lipid-infusion. Such labels may be identified for measuring "lipids" or "TPN" (i.e., total parenteral nutrition), as shown by status indicator 292. 48 hours may be recorded and displayed on a label attached to any portion of an IV set if directed by the policy of the particular facility in which the label is being used. 72 hours may be recorded and displayed on a label attached to any portion of an IV set or other vascular access device in accordance with infusion safety standards and recommendations of the Infusion Nurses Society. And, 96 hours may be recorded and displayed on a label attached to any portion of an IV set or other vascular access device in accordance with guidelines by the Center for Disease Control.

After a change in environment, physical use, or time has occurred, the status indicators will display a visible change, for example, by darkening or coloring at least a portion of the status indicators 292, 294, 296, 298, 300, 302, 304, and/or 306 until such change is ultimately shown as represented in the final condition 310 for each status indicator 292, 294, 296, 298, 300, 302, 304, and/or 306. Such visual change may occur as a rapid change from one color to another, as shown by comparing the initial condition 308 with the final condition 310 of status indicators 292, 294, 296, 298, and 300 and as represented in the graph of FIG. 22. Such visual change may occur as a rapid change at specific time intervals, as shown by comparing the initial condition 308 with the final condition 310 of status indicator 304. Such visual change may occur as a darkened word 312 such as "REPLACE", as shown by comparing the initial condition 308 with the final condition 310 of status indicator 306.

Such visual change may occur as a gradual, gradient, color change indicating a gradual change in environment, physical use, or time, as shown by comparing the initial condition 308 with the final condition 310 of status indicator 302. As shown in the final condition 310 of status indicator 302, a portion representing a period of 24 hours is completely darkened, indicating that a passage of 24 hours has certainly occurred, and a portion representing period of 96 hours has not darkened to any degree, indicating that a period of 96 hours has certainly not occurred. A majority of the portion representing a period of 48 hours is darkened, indicating that a period of 48 hours has likely occurred, and a minority of a portion representing a period of 72 hours is darkened, indicating that a period of 72 hours has not likely occurred. Status indicator 302, as shown in final condition, is not necessarily in final condition. That is, after a period of 96 hours has elapsed, status indicator 302 should be entirely darkened in its final condition.

A health care provider may attach or replace any one or more labels or status indicators to any vascular access device, and/or the labels or status indicators may be already secured to or integral to the devices prior to access by the health care provider.

Figure 44:
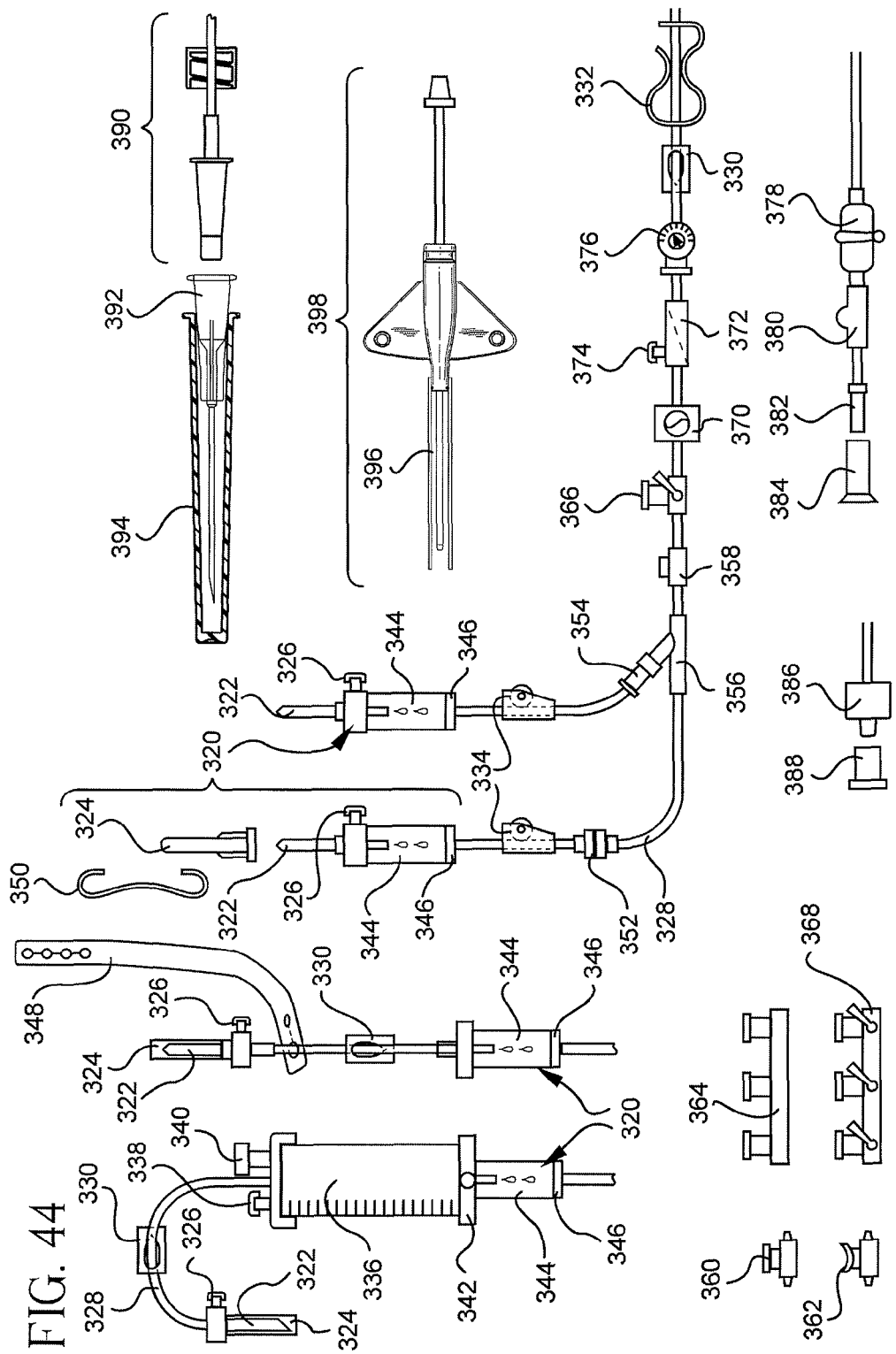
FIG. 44 is a schematic of various vascular access devices.

As discussed herein, a vascular access device, such as device 10, may include any device capable of providing therapy to the vascular system of a patient. Various examples of vascular access devices are provided herein. By way of further example and with reference to FIG. 44, a vascular access device may include any one or more of the following structures, taken alone or in any combination, and any other structure in communication with any of the following structures: an IV and/or drip chamber assembly 320 including a spike 322, a spike cover 324, a vent such as a spike vent 326, a cannula or catheter 328, a clamp including a slide clamp 330, a snap clamp 332, or a roller clamp 334, a burette 336, a burette vent 338, a burette fill port 340, a drug run prevention barrier 342, a drip chamber 344, a filter 346, a safety strap 348, an IV hook 350, a valve such as a check valve 352, an injection site and/or Luer connector 354, a Y-port 356, an access port including a needle access port 358, a blunt can access port 360, a Luer access port 362, a T-site manifold 364, a stop cock 366, or a stop cock manifold 368, a pump including a pump cartridge 370, an air or particulate filter 372 including a vent 374, a flow regulator 376 such as a precision flow regulator, a flash bulb 378, an air trap 380, a slip Luer 382, a cap such as a dust cap 384, a Luer lock 386, a vent cap 388, a universal Luer 390, a needle tip cannula 392 or catheter tip cannula, a needle tip guard or shield 394 or catheter tip guard or shield 396, and/or a needle set such as a wing needle set 398.

Hundreds, if not thousands, of vascular access devices exist or may be developed in the future. The vascular access devices described herein form merely an abbreviated list of some vascular access devices to which the principles and elements of the claimed invention may be applied. The principles and elements of the claimed invention may be applied to any structure discussed above, to its equivalents, or to similar, after-arising technology. Specifically, a status indicator may be placed in communication with any vascular access device to detect and/or communicate an event or passage of time helpful to a caregiver, such as the passage of time during which the device has been in use, an amount of usage of the device, whether or not the device has been cleaned, disinfected, or sterilized, and/or whether and to what extent one or more pathogens reside at or near the device.

Many of the embodiments discussed above have been described to include either reversible or non-reversible changes of status indicators. For example, a color change from a first color to a second color may reverse from the second color to the first color after a period of time or the occurrence of a certain event. Although not every example of reversible status indicators has been provided here, any claimed embodiment, whether described as reversible or non-reversible, or described without respect to reversibility, may be capable of reversing from a second state back to a first state or from a second state to an additional third state and is intended to come within the scope of the claimed invention.

The present invention may be embodied in other specific forms without departing from its structures, methods, or other essential characteristics as broadly described herein and claimed hereinafter. For example, the elements discussed above may be combined in any number and orientation in an enabling manner with any number and orientation of any of the other elements discussed above to produce a status indicator for a vascular access device. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A medical device, comprising:
   a vascular access device for communicating with the vascular system of a patient, wherein the vascular access device comprises:
   a body with a lumen;
   a status indicator comprising a moveable member movable from a first position to a second position, wherein movement of the moveable member from the first position to the second position provides an indication of elapsed time from when the vascular access device was placed in use in an intravenous access system;
   a septum coupled to the vascular access device; and
   a second status indicator disposed on the septum and being selected from a group consisting of a thermochromic material, a pH sensor, an alcohol sensor, and a colored substrate.

2. a vascular access device for communicating with the vascular system of a patient, wherein the vascular access device comprises;
   a body with a lumen;
   a status indicator including a moveable member movable from a first position to a second position within the body;

an attachment structure that attaches the movable member to the body in the first position for approximately a predetermined amount of time during the use of the vascular access device; and a spring in mechanical communication with the movable member for urging the movable member from the first position to the second position.

3. The medical device of claim 2, wherein the attachment structure includes a time sensitive adhesive.

4. The medical device of claim 2, wherein after approximately a predetermined amount of time during the use of the vascular access device in an intravenous access system the attachment structure releases the movable member, allowing the movable member to move from the first to the second position.

5. The medical device of claim 1 further comprising an opening in the body.

6. The medical device of claim 5 wherein the moveable member is viewable through the opening in the body.

7. The medical device of claim 6 further comprising a spring in mechanical communication with the moveable member for urging the moveable member from the first position to the second position.

8. A medical device, comprising:

a vascular access device for communicating with the vascular system of a patient, wherein the vascular access device comprises;

a body with a lumen, the body having an opening; and a status indicator comprising a moveable member movable from a first position to a second position to provide an indication of elapsed time from when the vascular access device was placed in use in an intravenous access system, the moveable member being viewable through an opening in the body, a spring being in mechanical communication with the moveable member for urging the moveable member from a first position to a second position, and a time sensitive adhesive attached to the moveable member that temporarily resists the force of the spring.

9. The medical device of claim 7 further comprising snap arms which hold the moveable member and temporarily resists the force of the spring.

10. The medical device of claim 7 further comprising a clamp which holds the moveable member and temporarily resists the force of the spring.

11. The medical device of claim 1, wherein the attachment structure includes a time sensitive adhesive.

12. The medical device of claim 1, further comprising an opening in the body of the vascular access device positioned on the body so that the moveable member is viewable through the opening in the body.

* * * * *